United States Patent
Semenza (12)

(10) Patent No.: US 6,562,799 B1
(45) Date of Patent: *May 13, 2003

(54) STABLE HYPOXIA INDUCIBLE FACTOR-1α AND METHOD OF USE

(75) Inventor: Gregg L. Semenza, Towson, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/383,581

(22) Filed: Aug. 25, 1999

Related U.S. Application Data

(63) Continuation-in-part of application No. 09/148,547, filed on Aug. 25, 1998, now Pat. No. 6,124,131.

(51) Int. Cl.[7] .......................... A61K 31/70; C07H 21/04; C12N 15/63; C12N 15/74; C12N 15/00

(52) U.S. Cl. ...................... 514/44; 435/320.1; 435/455; 435/375; 435/471; 536/23.1; 536/235

(58) Field of Search ...................... 514/44; 435/320.1, 435/455, 456, 458, 459, 471, 375; 536/23.1, 23.5

(56) References Cited

U.S. PATENT DOCUMENTS

| | | | |
|---|---|---|---|
| 5,882,914 A | 3/1999 | Semenza | 435/252.3 |
| 6,124,131 A | * 9/2000 | Semenza | 435/325 |

FOREIGN PATENT DOCUMENTS

| | | | |
|---|---|---|---|
| WO | WO 96/39426 | 12/1996 | C07K/14/00 |
| WO | WO 99/28469 | 10/1999 | C12N/15/12 |

OTHER PUBLICATIONS

Wivel et. al; Methods of Gene Delivery, 1998, Hematology/Oncology Clinics of North America, vol. 12, No. 3: 483–501.*

Dang et. al.; Gene Therapy and Translational Cancer Research, 1999, Clinical Cancer Research, vol. 5: 471–474.*

Deonarain; Ligand–targeted receptor–mediated vectors for gene delivery, 1998, Exp. Opin. Ther. Patents 8(1): 53–69.*

Romano et.al.: Latest Development in Gene Transfer Technology: Achievements, Perspectives, and Controversies over Therapeutic Applications, 2000, Stem Cells, 18: 19–39.*

Filion et.al.: Major Limitations in the use of cationic Liposomes for DNA delivery, 1997, International Journal of Pharmaceutics 162: 159–170.*

Blancher et.al.; The molecular basis of the hypoxia response pathway: Tumor hypoxia as a therapy target, 1998, Cancer and Metastasis Reviews 17: 187–194.*

Fujiwara et al., "Expressed Sequence Tag (EST), GenBank Accession No. D56430, D53682, R71408, T32121, HS14513, T32145, T35966, M85743, R71117, T32012, and Q60265," GenBank, May 30, 1995, see sequence alignments.

Benjamin et al., "Activation of the heat shock transcription factor by hypoxia in mammalian cells," *Proc. Natl. Acad. Sci. USA* 87:6263–6267 (Aug. 1990).

Wang et al., "Hypoxia–inducible factor 1 is a basic–helix––loop–helix–PAS heterodimer regulated by cellular $O_2$ tension," *Proc. Natl. Acad. Science USA* 92:5510–5514 (Jun. 1995).

Norris et al., "Hypoxia–induced Protein Binding to $O_2$–responsive Sequences on the Tyrosine Hydroxylase Gene," *The Journal of Biological Chemistry* 270:23774–23779 (Oct. 6, 1995).

Dejgaard et al., "Identification, Molecular Cloning, Expression and Chromosome Mapping of a Family of Transformation Upregulated hnRNP–K Proteins Derived by Alternative Splicing ," *J. Mol. Biol.* 236:33–48 (1994).

Verma et al., "Gene therapy—promises, problems and prospects," *Nature* 389:239–241 (Sep. 18, 1997).

Miller et al., "Targeted vectors for gene therapy," *FASEB* 9:190–199 (1995).

Eck et al., *Goodman and Gilman's The Pharmacological Basis of Therapeutics* (NY): McGraw–Hill, Chap. 5, pp. 81–82 (1995).

Levy, Andrew P. et al., "Transcriptional Regulation of the Rat Vascular Endothelial Growth Factor Gene by Hypoxia," *The Journal of Biological Chemistry*, vol. 270, No. 22, Jun. 2, 1995, pp. 13333–13340.

Semenza, Gregg L. et al., "Transcriptional Regulation of Genes Encoding Glycolytic Enzymes by Hypoxia–inducible Factor 1," *The Journal of Biological Chemistry*, vol. 269, No. 38, Sep. 23, 1994, pp. 23757–23763.

Wang, Guang L. et al., "General Involvement of Hypoxia–inducible Factor 1 in Transcriptional Response to Hypoxia," *Proc. Natl. Acad. Sci. USA*, vol. 90, May 1993, pp. 4304–4308.

Wang, Guang L. et al., "Purification and Characterization of Hypoxia–inducible Factor 1," *The Journal of Biological Chemistry*, vol. 270, No. 3, Jan. 20, 1995, pp. 1230–1237.

* cited by examiner

Primary Examiner—Dave T. Nguyen
Assistant Examiner—Quang Nguyen
(74) Attorney, Agent, or Firm—Gray Cary Ware & Freidenrich, LLP; Lisa A. Haile; Richard J. Imbra

(57) ABSTRACT

Substantially purified stable human hypoxia-inducible factor-1α (sHIF-1alpha) proteins and polynucleotides encoding stable human hypoxia-inducible factor-1α proteins are provided. A method is provided for treating a hypoxia-related tissue damage in a subject by administering to the subject a therapeutically effective amount of a sHIF-1alpha protein or a nucleic acid encoding a stable HIF-1alpha protein. Formulations are provided for the administration of stable human hypoxia inducible factor-1α (HIF-1alpha) polypeptide or a polynucleotide encoding stable human hypoxia inducible factor-1alpha (HIF-1alpha) to a patient having or at risk of having hypoxia- or ischemia-related tissue damage.

26 Claims, 10 Drawing Sheets

```
TAT GTG GAT AGT GAT ATG GTC AAT GAA TTC
tyr val asp ser asp met val asn glu phe
TTA GCT CCC TAT ATC CCA ATG GAT GAT GAC
leu ala pro tyr ile pro met asp asp asp
TTC CAG CAG ACT CAA ATA CAA GAA CCT ACT
phe gln gln thr gln ile gln glu pro thr
CCA TCT CCT ACC CAC ATA CAT AAA GAA ACT
pro ser pro thr his ile his lys glu thr
AAA TCT CAT CCA AGA AGC CCT AAC GTG TTA
lys ser his pro arg ser pro asn cal leu
ATG GAA CAT GAT GGT TCA CTT TTT CAA GCA
met glu his asp gly ser leu phe gln ala
GAA CAG AAT GGA ATG GAG CAA AAG ACA ATT
glu gln asn gly met glu gln lys thr ile
GTT AAT GCT CCT ATA CAA GGC AGC AGA AAC
val asn ala pro ile gln gly ser arg asn
AGTCTATTTATATTTCTACATCTAATTTTAGAAGCCTGG
```

```
TTTTTGGTATTTAAACCATTGCATTGCAGTAGCATCATT
CATAGGCAGTTGAAAAATTTTTACACCTTTTTTTTCACA
TTAAGAAGAAATTTTTTTTGGCCTATGAAATTGTTAAAC
GGCATTTATTTGGATAAAATTCTCAATTCAGAGAAATCA
GTATAAGATATTTTGAGCAGACTGTAAACAAGAAAAAA
TAATTTTAGAAGCATTATTTAGGAATATATAGTTGTCA
AAAAAAAAAAAAAAAAAAAAAAAAAAAAAAAAAAAAA
```

FIG. 1A

| | | | | | | | | |
|---|---|---|---|---|---|---|---|---|
| GAG | CCT | AAT | AGT | CCC | AGT | GAA | TAT | TGT | TTT |
| glu | pro | asn | ser | pro | ser | glu | tyr | sys | phe |
| ACT | CAG | GAC | ACA | GAT | TTA | GAC | TTG | GAG | ATG |
| thr | gln | asp | thr | asp | leu | asp | leu | glu | met |
| AGC | GCA | AGT | CCT | CAA | AGC | ACA | GTT | ACA | GTA |
| ser | ala | ser | pro | gln | ser | thr | val | thr | val |
| ATG | GAA | GAC | ATT | AAA | ATA | TTG | ATT | GCA | TCT |
| met | glu | asp | ile | lys | ile | leu | ile | ala | ser |
| GCA | GGA | AAA | GGA | GTC | ATA | GAA | CAG | ACA | GAA |
| ala | gly | lys | gly | val | ile | glu | gln | thr | glu |
| GCT | TTG | CAG | AAT | GCT | CAG | AGA | AAG | CGA | AAA |
| ala | leu | gln | asn | ala | gln | arg | lys | arg | lys |
| TGG | AAA | CGT | GTA | AAA | GGA | TGC | AAA | TCT | AGT |
| trp | lys | arg | val | lys | gly | cys | lys | ser | ser |
| TTA | CCA | CAG | CTG | ACC | AGT | TAT | GAT | TGT | GAA |
| leu | pro | gln | leu | thr | ser | tyr | asp | cys | glu |

CATTCCTTTTTTTGGACACTGGTGGCTCACTACCTAAAGC

TGTTCTTTAATGCTGGATCACAGACAGCTCATTTTCTCAGT
AATATAATTTTTGTAAGAAGGCAGTAACCTTTCATCATGAT
AGTTACTCATGGAATATATTCTGCGTTTATAAAACTAGTTT
TACATAATATAGAAGATATGCATATATCTAGAAGGTATGT
TGTAACTGATATTAAACCTAAATGTTCTGCCTACCCTGTTG
CTATTAACATCCTTTTTTTCATGTAGATTTCAATAATTGAG
ACTGTATTGTTTTGTTACATCAAATAAACATCTTCTGTGGA

FIG. 1B

```
TCC GAT GGA AGC ACT AGA CAA AGT TCA CCT
ser asp gly ser thr arg gln ser ser pro
GAA GAC ACA GAA GCA AAG AAC CCA TTT TCT
glu asp thr glu ala lys asn pro phe ser
CCA TTA GAA AGC AGT TCC GCA AGC CCT GAA
pro leu glu ser ser ser ala ser pro glu
GAT GAA TTA AAA ACA GTG ACA AAA GAC CGT
asp glu leu lys thr val thr lys asp arg
ACT CAA AGT CGG ACA GCC TCA CCA AAC AGA
thr gln ser arg thr ala ser pro asn arg
CCT GAG GAA GAA CTA AAT CCA AAG ATA CTA
pro glu glu glu leu asn pro lys ile leu
GAC GAT CAT GCA GCT ACT ACA TCA CTT TCT
asp asp his ala ala thr thr set leu ser
CTG CTG GGG CAA TCA ATG CAT GAA AGT GGA
leu leu gly gln ser met asp glu ser gly
TTG GAT CAA GTT AAC TGA GCTTTTTCTTAATTT
leu asp gln val asn OPA
CCCCTTTCTACTTAATTTACATTAATGCTCTTTTTTAGTA
GGAGTTTATCCCTTTTCGAATTATTTTTAAGAAGATGCC
AGCCACAATTGCACAATATATTTTCTTAAAAAATACCAGC
AAATGCTGTATGGTTTATTATTTAAATGGGTAAAGCCATT
ACAATACCCTATGTAGTTGTGGAAGTTTATGCTAATATTG
TTTGCTCAAAATACAATGTTTGATTTTATGCACTTTGTCG
TTTTCATTCCTTTTGCTCTTTGTGGTTGGATCTAACACTA
```

FIG. 1C

| | | | | | | | | | |
|---|---|---|---|---|---|---|---|---|---|
|1502|CCC|CAG|ATT|CAG|GAT|CAG|ACA|CCT|AGT|CCT|
| 492|pro|gln|ile|gln|asp|gln|thr|pro|ser|pro|
|1622|AAG|TTG|GAA|TTG|GTA|GAA|AAA|CTT|TTT|GCT|
| 532|lys|leu|glu|leu|val|glu|lys|leu|phe|ala|
|1742|TTC|CAG|TTA|CGT|TCC|TTC|GAT|CAG|TTG|TCA|
| 572|phe|gln|leu|arg|ser|phe|asp|gln|leu|ser|
|1862|GCT|AAT|GCC|ACC|ACT|ACC|ACT|GCC|ACC|ACT|
| 612|ala|asn|ala|thr|thr|thr|thr|ala|thr|thr|
|1982|ACT|AGT|GCC|ACA|TCA|TCA|CCA|TAT|AGA|GAT|
| 652|thr|ser|ala|thr|ser|ser|pro|tyr|arg|asp|
|2102|TCT|GTC|GCT|TTG|AGT|CAA|AGA|ACT|ACA|GTT|
| 692|ser|val|ala|leu|ser|gln|arg|thr|thr|val|
|2222|GTA|GGA|ATT|GGA|ACA|TTA|TTA|CAG|CAG|CCA|
| 732|val|gly|ile|gly|thr|leu|leu|gln|gln|pro|
|2342|ATT|TTA|ATA|CCC|TCT|GAT|TTA|GCA|TGT|AGA|
| 772|<u>ile</u>|<u>leu</u>|<u>ile</u>|<u>pro</u>|<u>ser</u>|<u>asp</u>|<u>leu</u>|<u>ala</u>|<u>cys</u>|<u>arg</u>|
|2462|CTA|CTG|CAG|GGT|GAA|GAA|TTA|CTC|AGA|GCT|
| 812|leu|leu|gln|gly|glu|glu|leu|leu|arg|ala|

```
2605 CTACAATACTGCACAAACTTGGTTAGTTCAATTTTTGAT
2764 TTAAAAAATGCACCTTTTTATTTATTTATTTTTGGCTAG
2923 TTTTACATAAATAATAATGCTTTGCCAGCAGTACGTGGT
3082 CTGGAACATGACATTGTTAATCATATAATAATGATTCTT
3241 TCTGATGTTTCTATAGTCACTTTGCCAGCTCAAAAGAAA
3400 AAAATCATGCATTCTTAGCAAAATTGCCTAGTATGTTAA
3559 CAGTAAATATCTTGTTTTTCTATGTACATTGTACAAAT
```

FIG. 1D

```
GCG GGC GCC GGC GGC GCG AAC GAC AAG AAA
glu gly ala gly gly ala asn asp lys lys
CAT CAG TTG CCA CTT CCA CAT AAT GTG AGT
his gln leu pro leu pro his asn val ser
GAT GAC ATG AAA GCA CAG ATG AAT TGC TTT
asp asp met lys ala gln met asn cys phe
TTA ACT CAG TTT GAA CTA ACT GGA CAC AGT
leu thr gln phe glu leu thr gly his ser
AAC ACA CAG CGA AGC TTT TTT CTC AGA ATG
asn thr gln arg ser phe phe leu arg met
GAT ACC AAC AGT AAC CAA CCT CAG TGT GGG
asp thr asn ser asn gln pro gln cys gly
TTC CTC AGT CGA CAC AGC CTG GAT ATG AAA
phe leu ser arg his ser leu asp met lys
TTG GAC TCT GAT CAT CTG ACC AAA ACT CAT
leu asp ser asp his leu thr lys thr his
ACT GTC ATA TAT AAC ACC AAG AAT TCT CAA
thr val ile tyr asn thr lys asn ser gln
AAA CCG GTT GAA TCT TCA GAT ATG AAA ATG
lys pro val glu ser ser asp met lys met
CCA GCC GCT GGA GAC ACA ATC ATA TCT TTA
pro ala ala gly asp thr ile ile ser leu
AAA TTA CAG AAT ATA AAT TTG GCA ATG TCT
lys leu gln asn ile asn leu ala met ser
CCA GAG TCA CTG GAA CTT TCT TTT ACC ATG
pro glu ser leu glu leu ser phe thr met
```

*FIG. 1E*

```
                              GTGAAGACATCGCGGGGACCGATTCACC ATG
                                                           met
AAA GAA TCT GAA GTT TTT TAT GAG CTT GCT
lys glu ser glu val phe tyr glu leu ala
CTT CTG GAT GCT GGT GAT TTG GAT ATT GAA
leu leu asp ala gly asp leu asp ile glu
ATT TCT GAT AAT GTG AAC AAA TAC ATG GGA
ile ser asp asn val asn lys tyr met gly
AAT GGC CTT GTG AAA AAG GGT AAA GAA CAA
asn gly leu val lys lys gly lys glu glu
TTG CAC TGC ACA GGC CAC ATT CAC GTA TAT
leu his cys thr gly his ile his val tyr
AAT ATT GAA ATT CCT TTA GAT AGC AAG ACT
asn ile glu ile pro leu asp ser lys thr
GGC CGC TCA ATT TAT GAA TAT TAT CAT GCT
gly arg ser ile tyr glu tyr tyr his ala
GGT GGA TAT GTC TGG GTT GAA ACT CAA GCA
gly gly tyr val trp val glu thr gln ala
TTC TCC CTT CAA CAA ACA GAA TGT GTC CTT
phe ser leu gln gln thr glu cys val leu
AAG GAA CCT GAT GCT TTA ACT TTG CTG GCC
lys glu pro asp ala leu thr leu leu ala
AAT GAT GTA ATG CTC CCC TCA CCC AAC GAA
asn asp val met leu pro ser pro asn glu
CAA GAA GTT GCA TTA AAA TTA GAA CCA AAT
gln glu val ala leu lys leu glu pro asn
```

FIG. 1F

```
TCT CGA GAT GCA GCC AGA TCT CGG CGA AGT
ser arg asp ala ala arg ser arg arg ser
CTT ACC ATC AGC TAT TTG CGT GTG AGG AAA
leu thr ile ser tyr leu arg val arg lys
GTT CTC ACA GAT GAT GGT GAC ATG ATT TAC
val leu thr asp asp gly asp met ile tyr
GAG GAA ATG AGA GAA ATG CTT ACA CAC AGA
glu glu met arg glu met leu thr his arg
ATG AAC ATA AAG TCT GCA ACA TGG AAG GTA
met asn ile lys ser ala thr trp lys val
CTG ATT TGT GAA CCC ATT CCT CAC CCA TCA
leu ile cys glu pro ile pro his pro ser
TTG ATG GGA TAT GAG CCA GAA GAA CTT TTA
leu met gly tyr glu pro glu glu leu leu
ACA GGA CAG TAC AGG ATG CTT GCC AAA AGA
thr gly gln tyr arg met leu ala lys arg
GTG AGT GGT ATT ATT CAG CAC GAC TTG ATT
val ser gly ile ile gln his asp leu ile
GAT ACA AGT AGC CTC TTT GAC AAA CTT AAG
asp thr ser ser leu phe asp lys leu lys
GAC CAG CAA CTT GAG GAA GTA CCA TTA TAT
asp gln gln leu glu glu val pro leu tyr
CTT CGA AGT AGT GCT GAC CCT GCA CTC AAT
leu arg ser ser ala asp pro ala leu asn
```

FIG. 1G

```
   1
   1
  62 AAG ATA AGT TCT GAA CGT CGA AAA GAA AAG
  12 lys ile ser ser glu arg arg lys glu lys
 182 TCG CAT CTT GAT AAG GCC TCT GTG ATG AGG
  52 ser his leu asp lys ala ser val met arg
 302 TAT TTG AAA GCC TTG GAT GGT TTT GTT ATG
  92 tyr leu lys ala leu asp gly phe val met
 422 GTG TTT GAT TTT ACT CAT CCA TGT GAC CAT
 132 val phe asp phe thr his pro cys asp his
 542 AAG TGT ACC CTA ACT AGC CGA GGA AGA ACT
 172 lys cys thr leu thr ser arg gly arg thr
 662 TAT AAG AAA CCA CCT ATG ACC TGC TTG GTG
 212 tyr lys lys pro pro met thr cys leu val
 782 TTT TCT TAT TGT GAT GAA AGA ATT ACC GAA
 252 phe ser tyr cys asp glu arg <u>ile thr glu</u>
 902 CAT GAT ATG TTT ACT AAA GGA CAA GTC ACC
 292 his asp met phe thr lys gly gln val thr
1022 CCA CAG TGC ATT GTA TGT GTG AAT TAC GTT
 332 pro gln cys ile val cys val asn tyr val
1142 ACT CAG CTA TTC ACC AAA GTT GAA TCA GAA
 372 thr gln leu phe thr lys val glu ser glu
1262 GAT TTT GGC AGC AAC GAC ACA GAA ACT GAT
 412 asp phe gly ser asn asp thr glu thr asp
1382 CCA TTA CCC ACC GCT GAA ACG CCA AAG CCA
 452 pro leu pro thr ala glu thr pro lys pro
```

FIG. 1H

| | RESIDUES | REGULATION |
|---|---|---|
| ←bHLH-PAS→     ←TADS→ | 1-826 | + |
| | 1-754 | + |
| | 1-729 | + |
| | 1-726 | + |
| | 1-703 | − |
| | 1-681 | − |
| | 1-608 | − |
| | 1-390 | − |

| | RESIDUES | REGULATION | |
|---|---|---|---|
| | | Wt | mut |
| ←bHLH-PAS→     ←TADS→ | 1-826 | + | + |
| | 1-390 | − | |
| | 1-391, 429-826 | + | − |
| | 1-391, 469-826 | + | − |
| | 1-391, 494-826 | + | − |
| | 1-391, 508-826 | + | − |
| | 1-391, 512-826 | + | − |
| | 1-391, 517-826 | + | − |
| | 1-391, 521-826 | − | |
| | 1-391, 549-826 | − | |
| | 1-391, 576-826 | − | |

STABLE HYPOXIA INDUCIBLE FACTOR-1α AND METHOD OF USE

RELATED APPLICATIONS

This application is a continuation-in-part of application U.S. Ser. No. 09/148,547, filed Aug. 25, 1998, now U.S. Pat. No. 6,124,131.

STATEMENT AS TO FEDERALLY SPONSORED RESEARCH

This invention was made in part with funds from the National Heart, Lung, and Blood Institute, grant number 1R01-HL55338. The government may have certain rights in this invention.

FIELD OF THE INVENTION

This invention relates generally to hypoxia-inducible DNA-binding proteins and more specifically to DNA binding proteins that are modified such that they are stable under non-hypoxic as well as hypoxic conditions.

BACKGROUND OF THE INVENTION

Mammals require molecular oxygen ($O_2$) for essential metabolic processes including oxidative phosphorylation in which $O_2$ serves as electron acceptor during ATP formation. Systemic, local, and intracellular homeostatic responses elicited by hypoxia (the state in which $O_2$ demand exceeds supply) include erythropoiesis by individuals who are anemic or at high altitude (Jelkmann, *Physiol. Rev.* 72:449–489, 1992), neovascularization in ischemic myocardium (White et al., *Circ. Res.* 71:1490–1500, 1992), and glycolysis in cells cultured at reduced $O_2$ tension (Wolfe et al., *Eur. J. Biochem.* 135:405–412, 1983). These adaptive responses either increase $O_2$ delivery or activate alternate metabolic pathways that do not require $O_2$. Hypoxia-inducible gene products that participate in these responses include erythropoietin (EPO) (reviewed in Semenza, *Hematol. Oncol. Clinics N*.erythropoietin (EPO) (reviewed in Semenza, *Hematol. Oncol. Clinics N. Amer.* 8:863–884, 1994), vascular endothelial growth factor (VEGF) (Shweiki et al., *Nature* 359:843–845, 1992; Banai et al., *Cardiovasc. Res.* 28:1176–1179, 1994; Goldberg & Schneider, *J. Biol. Chem.* 269:4355–4359, 1994), and glycolytic enzymes (Firth et al., *Proc. Natl. Acad. Sci. USA* 91:6496–6500, 1994; Semenza et al., *J. Biol. Chem.* 269:23757–23763, 1994).

The molecular mechanisms that mediate genetic responses to hypoxia have been extensively investigated for the EPO gene, which encodes a growth factor that regulates erythropoiesis and thus blood $O_2$-carrying capacity (Jelkmann, 1992, supra; Semenza, 1994, supra). Cis-acting DNA sequences required for transcriptional activation in response to hypoxia were identified in the EPO 3'-flanking region and a trans-acting factor that binds to the enhancer, hypoxia-inducible factor 1 (HIF-1), fulfilled criteria for a physiological regulator of EPO transcription. In particular, inducers of EPO expression (1% $O_2$, cobalt chloride [$CoCl_2$], and desferrioxamine [DFX]) also induced HIF-1 DNA binding activity with similar kinetics. In addition, inhibitors of EPO expression (actinomycin D, cycloheximide, and 2-aminopurine) blocked induction of HIF-1 activity. Furthermore, mutations in the EPO 3'-flanking region that eliminated HIF-1 binding also eliminated enhancer function (Semenza, 1994, supra). These results support a signal transduction pathway requiring ongoing transcription, translation, and protein phosphorylation participates in the induction of HIF-1 DNA-binding activity and EPO transcription in hypoxic cells (Semenza, 1994, supra).

EPO expression is cell type specific, but induction of HIF-1 activity by 1% $O_2$, $CoCl_2$, or DFX was detected in many mammalian cell lines (Wang & Semenza, *Proc. Natl. Acad. Sci. USA* 90:4304–4308, 1993). The EPO enhancer directed hypoxia-inducible transcription of reporter genes transfected into non-EPO-producing cells (Wang & Semenza, 1993, supra; Maxwell et al., *Proc. Natl. Acad. Sci. USA* 90:2423–2427, 1993). RNAs encoding several glycolytic enzymes were induced by 1% $O_2$, $CoCl_2$, or DFX in EPO-producing Hep3B or nonproducing HeLa cells whereas cycloheximide blocked their induction and glycolytic gene sequences containing HIF-1 binding sites mediated hypoxia-inducible transcription in transfection assays (Firth et al., 1994, supra; Semenza et al., 1994, supra). These experiments support the role of HIF-1 in activating homeostatic responses to hypoxia.

Hypoxia inducible factor-1(HIF-1) is a mammalian transcription factor expressed uniquely in response to physiologically relevant levels of hypoxia (Wang, G. L., et al., *Proc. Natl. Acad. Sci. USA* 92:5510–5514, 1995; Wang, G. L., and Semenza, G. L., *J. Biol. Chem.* 270:1230–1237, 1995; U.S. Pat. No. 5,882,914). HIF-1 is a basic helix loop-helix protein that binds to cis-acting hypoxia-responsive elements of genes induced by hypoxia (Wang, G. L., and Semenza, G. L., *Curr. Opin. Hematol.* 3:156–162, 1992; Jiang, B. H., et al., *J. Biol. Chem.* 212:19253–19260, 1997). The genes that are activated by HIF-1 in cells subjected to hypoxia include EPO, vascular endothelial growth hormone (VEGF), heme oxygenase-1, inducible nitric oxide synthase, and glycolytic enzymes aldolase A, enolase 1, lactate dehydrogenase A, phosphofructokinase I, and phosphoglycerate kinase 1 (Semenza, G. L., et al., *Kid. Int.* 51:553–555, 1997). HIF-1 DNA binding activity and HIF-1 protein concentration increase exponentially as cells are subjected to decreasing $O_2$ concentrations (Jiang, B. H., et al., *Am J. Physiol.* 271:C 172-C1180, 1996).

HIF-1 also activates transcription of the VEGF gene in hypoxic cells (Forsythe et al., 1996; Iyer et al., 1998). When cultured cells are transfected with pCEP4/HIF-1alpha plasmid under conditions that allow expression of HIF-1alpha from a cytomegalovirus promoter and a reporter plasmid containing the hypoxia response element from the VEGF gene, reporter gene expression is increased in cells under non-hypoxic conditions and there is a dramatic superinduction under hypoxic conditions that is dependent upon the presence of an intact HIF-1 binding site (Forsythe et al., 1996). In embryonic stem cells from a knockout mouse, which lack HIF-1alpha expression, there is no expression of VEGF mRNA in response to hypoxia (Iyer et al., 1998).

HIF-1 is a heterodimer of two subunits, HIF-1alpha and HIF-1beta. The HIF-1alpha subunit is unique to HIF-1, whereas HIF-1beta (also known as aryl hydrocarbon receptor nuclear translocator, ARNT) can dimerize with other proteins. The concentration of HIF-1alpha and HIF-1beta RNA and HIF-1alpha and HIF-1beta polypeptide increases in cells exposed to hypoxic conditions (Wiener, C. M., et al., *Biochem. Biophys. Res. Commun.* 225:485–488, 1996; Yu, A. Y., et al., *Am J. Physiol.* 275:L818–L826, 1998).

Structural analysis of HIF-1alpha revealed that dimerization requires two domains, termed HLH and PAS. DNA binding is mediated by a basic domain (Semenza, G. L., et al., *Kid. Int.* 51:553–555, 1997). Two transactivation domains are contained in HIF-1alpha, located between amino acids 531 and 826. The minimal transactivation domains are at amino acid residues 531–575 and 786–826 (Jiang, B. H., et al., 1997, supra; Semenza, G. L., et al., 1997, supra). Amino acids 1–390 are required for optimal heterodimerization with HIF1beta (ARNT) and DNA binding. In addition, deletion of the carboxy terminus of HIF-1alpha (amino acids 391–826) decreased the ability of HIF-1 to activate transcription. However, HIF-1alpha (1–390) was expressed at high levels in both hypoxic and non-hypoxic cells in contrast to full-length HIF-1alpha (1–826) which was expressed at much higher levels in hypoxic relative to non-hypoxic cells (Jiang, B.-H., et al., *J. Biol. Chem.* 271:17771–17778, 1996). Thus, hypoxia has two independent effects on HIF-1alpha activity: (1) hypoxia increases the steady-state levels of HIF-1alpha protein by stabilizing it (i.e. decreasing its degradation); and (2) hypoxia increases the specific transcriptional activity of theprotein (i.e. independent of the protein concentration).

SUMMARY OF THE INVENTION

This invention is based on the discovery and isolation of unique variant forms of HIF-1alpha polypeptide that are stable under hypoxic and nonhypoxic conditions. The invention further includes chimeric proteins having HIF-1alpha DNA binding domain and dimerization domains and a heterologous transactivation domain. Given the structural and functional similarities between HIF-1alpha , HIF-2alpha (also known as EPAS 1, HLF, HRF, and MOP2), and HIF-3alpha (see Gu, Y.-Z., et al., Gene Expr. 7:205–213, 1998) it is understood that HIF-1alpha is described for illustrative purposes, but that all these HIFs are included herein.

A stable HIF-1alpha (sHIF-1alpha ) protein of the invention includes the following properties: (1) sHIF-1alpha will contain the basic-helix-loop-helix-PAS domain of HIF-1alpha that mediates dimerization with HIF-1beta (ARNT) and binding to HIF-1 recognition sites on DNA, e.g., the sequence 5'-TACGTGCT-3' from the human EPO gene (which was used to purify HIF-1 originally) or the sequence 5'-TACGTGGG-3' from the human VEGF gene (Forsythe et al., 1996; Semenza and Wang, Mol. Cell. Biol. 12:5447–5454, 1992); (2) sHIF-1alpha will contain deletions or amino acid substitutions that substantially increase its half-life in cells under non-hypoxic conditions such that the sHIF-1alpha protein accumulates to much higher levels than the wild-type HIF-1alpha protein under these conditions. There are many different deletions and/or amino acid substitutions that will result in this effect; multiple examples are provided but these are not limiting; (3) sHIF-1alpha contains one or more transcriptional activation domains derived either from HIF-1alpha or another eukaryotic or viral transcription factor. Depending on the activation domain utilized, the transcriptional activity of sHIF-1alpha may be regulated by oxygen concentration or may be constitutively active regardless of oxygen concentration. sHIF-1alpha mediates increased transcription of hypoxia-inducible genes normally regulated by HIF-1.

In one embodiment, the invention includes an isolated nucleic acid sequence encoding a stable HF-1alpha protein that is a chimeric transactivator. This chimeric transactivator includes: a) a nucleotide sequence encoding a DNA binding domain and a dimerization domain of a hypoxia inducible factor (e.g., HIF-1alpha, HIF-2alpha, or HIF-3alpha); and b) a nucleotide sequence encoding a transcriptional activation domain. The preferred hypoxia inducible factor of the invention is HIF-1alpha.

In another embodiment, the invention provides non-chimeric stable HIF-1alpha polypeptides. Such polypeptides include, but are not limited to, HIF-1alpha amino acid residues 1–391 and 521–826 of SEQ ID NO:1; amino acid residues 1–391 and 549–826 of SEQ ID NO:1; amino acid residues 1–391 and 576–826 of SEQ ID NO:1; amino acid residues 1–391 and 429–826 of SEQ ID NO:1, wherein 551 is no longer serine and 552 is not threonine; amino acid residues 1–391 and 469–826 of SEQ ID NO:1, wherein 551 is no longer serine and 552 is not threonine; amino acid residues 1–391 and 494–826 of SEQ ID NO:1, wherein 551 is no longer serine and 552 is not threonine; amino acid residues 1–391 and 508–826 of SEQ ID NO:1, wherein 551 is no longer serine and 552 is not threonine; amino acid residues 1–391 and 512–826 of SEQ ID NO:1, wherein 551 is no longer serine and 552 is not threonine; and amino acid residues 1–391 and 517–826 of SEQ ID NO:1, wherein 551 is no longer serine and 552 is not threonine.

The invention further provides a method for providing constitutive expression of a hypoxia inducible factor in a cell, under hypoxic or non-hypoxic conditions. The method includes contacting the cell with a nucleic acid sequence encoding a chimeric transactivator protein as described herein, or a stable HIF-1alpha as described herein, under conditions that allow expression of the nucleic acid sequence, thereby providing constitutive expression of a hypoxia inducible factor.

The invention also provides a method for increasing expression of a hypoxia inducible gene in a cell. The method includes contacting the cell with an expression vector containing a polynucleotide encoding a stable HIF-1alpha of the invention or a chimeric transactivator protein as described herein under conditions that allow expression of the nucleic acid sequence contained in the vector thereby providing for increased expression of hypoxia inducible genes in the cell. Such genes include, for example, VEGF.

Further included in the invention is a method for reducing hypoxia or ischemia-related tissue damage in a subject having or at risk of having such damage. The method includes administering to the subject a therapeutically effective amount of a nucleic acid sequence encoding a chimeric transactivator protein as described herein, or a stable HIF-1alpha as described herein, in a pharmaceutically acceptable carrier, thereby inducing gene expression that will reduce, or prevent, or repair tissue damage. Examples of gene products whose expression is induced by sHIF-1alpha resulting in a therapeutic effect include VEGF and other mediators of angiogenesis and insulin-like growth factor 2 (IGF-2) and other factors promoting cell survival (Iyer et al., 1998; Feldser, D., et al., Cancer Res. 59:3915, 1999).

In another embodiment, the invention provides a method for providing prophylactic therapy for tissue in a subject in need thereof comprising administering to the subject an amount of a polypeptide encoded by a polynucleotide encoding a chimeric transactivator protein as described herein, or a stable HIF-1alpha as described herein, such that angiogenesis is induced at levels that are greater than before administration of the polypeptide, thereby providing prophylactic therapy.

In one embodiment, the invention provides a substantially purified polypeptide having a sequence as set forth in SEQ ID NO:1, wherein amino acids 392 to 428 are deleted therefrom, amino acid 551 is changed from a serine to any other amino acid, and amino acid 552 is changed from a threonine to any other amino acid. Isolated polynucleotides encoding such a polypeptide as well as antibodies which preferentially bind this polypeptide are also provided in a particular embodiment, serine 551 is changed to glycine and threonine 552 to alanine.

In one embodiment, a method is provided for treating a hypoxia-related tissue damage in a subject, by administering to the subject a therapeutically effective amount of a nucleotide sequence comprising an expression control sequence operatively linked to a polynucleotide encoding a polypeptide having a sequence as set forth in SEQ ID NO:1, wherein amino acids 392 to 428 are deleted therefrom, amino acid 551 is changed from a serine to any other amino acid, and amino acid 552 is changed from a threonine to any other amino acid.

In another embodiment, the invention provides a method of treating a hypoxia-related tissue damage in a subject by administering to the subject a therapeutically effective amount of a polypeptide having a sequence as set forth in SEQ ID NO:1, wherein amino acids 392 to 428 are deleted therefrom, amino acid 551 is changed from a serine to any other amino acid, and amino acid 552 is changed from a threonine to any other amino acid.

In a further embodiment, the invention provides a formulation for administration of stable human hypoxia inducible factor-1 (HIF-1alpha) polypeptide to a patient having hypoxia related tissue damage. The method includes a substantially pure polypeptide having a sequence as set forth in SEQ ID NO:1, wherein amino acids 392 to 428 are deleted therefrom, amino acid 551 is changed from a serine to any other amino acid, and amino acid 552 is changed from a threonine to any other amino acid; and a pharmaceutically acceptable carrier.

The invention also provides a formulation for administration of a polynucleotide encoding stable human hypoxia inducible factor-1 (HIF-1alpha) to a patient having hypoxia related tissue damage, including a therapeutically effective amount of a nucleic acid sequence comprising an expression control sequence operatively linked to a polynucleotide encoding a polypeptide having a sequence as set forth in SEQ ID NO:1, wherein amino acids 392 to 428 are deleted therefrom, amino acid 551 is changed from a serine to any other amino acid, and amino acid 552 is changed from a threonine to any other amino acid; and a pharmaceutically acceptable carrier.

BRIEF DESCRIPTION OF THE DRAWINGS

FIGS. 1A–H is the amino acid sequence (SEQ ID NO:1) of wild-type HIF-1alpha.

DETAILED DESCRIPTION OF THE INVENTION

Figures 2, 3, 4:
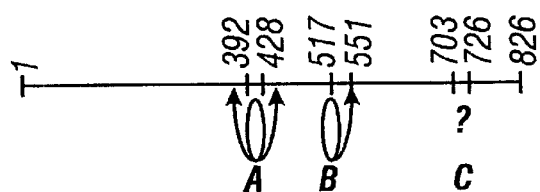
FIG. 2 shows an analysis of the effect of carboxyl-terminal deletions on the regulated expression of HIF-1alpha.
FIG. 3 shows an analysis of the effect of internal deletions on regulated expression of HIF-1alpha polypeptide. Oxygen regulation of the HIF-1alpha polypeptide containing the indicated internal deletion is shown in the "wt" column, where a "+" indicates that the polypeptide is regulated, and is therefore unstable under non-hypoxic conditions. Each of the indicated internal deletions in HIF-1alpha has been combined with a double point mutation (a serine to glycine mutation at amino acid 551 and a threonine to alanine mutation at residue 552). The oxygen regulation of the polypeptide containing both the indicated internal deletion and the double point mutation is shown in the "mut" column, where a "+" indicates that the polypeptide is regulated, and is therefore unstable under non-hypoxic conditions.
FIG. 4 shows a model of regulated expression of HIF-1alpha. Putative regulatory sequences identified within the HIF-1alpha protein by deletion analysis are indicated. Potential interactions with regulatory proteins such as a phosphatase, kinase, or protease are also shown.

It must be noted that as used herein and in the appended claims, the singular forms "a, "and, and "the" include plural referents unless the context clearly dictates otherwise. Thus, for example, reference to "a cell" includes a plurality of such cells and reference to "the plasmid" includes reference to one or more plasmids and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the cell lines, vectors, and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The invention provides a substantially pure stable hypoxia-inducible factor-1 (sHIF-1alpha) protein, or mutein. Wild-type, full-length HIF-1alpha is expressed at lower levels in nonhypoxic cells as compared to hypoxic cells (Wang, G. L., et al., *Proc. Natl. Acad. Sci. USA* 92:5510–5514, 1995; Wang, G. L., and Semenza, G. L., *J. Biol. Chem.* 270:1230–1237, 1995; Jiang, B. H., et al., *J. Biol. Chem.* 272:19253–19260, 1997, herein incorporated by reference) while sHIF-1alpha is stable under nonhypoxic as well as hypoxic conditions. Wild type HIF-1alpha and sHIF-1alpha are characterized as being able to form heterodimers with HIF-1beta to form a DNA-binding protein, hypoxia inducible factor-1 (HIF-1), a mammalian transcription factor. HIF-1 activates transcription of multiple genes including those encoding erythropoietin (EPO), vascular endothelial growth factor (VEGF), glucose transporters, and glycolytic enzymes.

The term "mutein" as used herein refers to a variant form of HIF-1alpha polypeptide that is stable under hypoxic or non-hypoxic conditions. HIF-1alpha polypeptide, upon dimerization with HIF-1beta, is a DNA binding protein, which is characterized as activating gene expression where the promoter region of the target gene contains a HIF-1 binding site (Semenza, G. L., et al., *Kid. Int.* 51:553–555, 1997; Iyer, N. V., et al., *Genes Dev.* 12:149–162, 1998, both herein incorporated by reference). Examples of such structural genes include erythropoietin (EPO), vascular endothelial growth hormone (VEGF) and glycolytic genes. HIF-1alpha migrates on SDS polyacrylamide gel electrophoresis with an apparent molecular mass of 120 kDa and has essentially the amino acid sequence as set forth in SEQ ID NO:1. The term HIF-1alpha includes the polypeptide as set forth in SEQ ID NO:1, and conservative variations of the polypeptide sequence. The term "conservative variant" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. In a referred embodiment, HIF-1alpha has the sequence as set forth in SEQ ID No:1. HIF-1alpha is described in detail in copending application U.S. patent application Ser. No. 08/480,473, herein incorporated by reference.

In general, a mutein will have an amino acid sequence that differs from the native sequence by including substitutions, insertions, and/or deletions for example). Muteins are easily prepared using modern cloning techniques, or may be synthesized by solid state methods by site-directed mutagenesis. A mutein may include dominant negative forms of a polypeptide.

The invention provides a substantially pure stable hypoxia-inducible factor-1 (sHIF-1alpha)mutein. sHIF-1alpha polypeptide has a sequence as set forth in SEQ ID NO:1, wherein amino acids 392 to 428 are deleted therefrom, amino acid 551 is changed from a serine to any other amino acid, and amino acid 552 is changed from a threonine to any other amino acid. In one embodiment, amino acids 392 to 428 are deleted from SEQ ID NO:1 and amino acid 551 is changed from a serine to a glycine. In another embodiment, amino acids 392 to 428 are deleted from SEQ ID NO:1 and amino acid 552 is changed from a threonine to an alanine. In yet another embodiment, amino acids 392 to 428 are deleted from SEQ ID NO:1 and amino acid 551 is changed from a serine to a glycine and amino acid 552 is changed from a threonine to an alanine.

Without being bound by theory, two regions of full-length HIF-1alpha have been identified that are important for stable expression of HIF-1alpha. Region AB is located from about amino acid 392 to amino acid 552. Within this region, two sequences A and B, have been identified. In particular, sequence A is from amino acid 392 to amino acid 428 of SEQ ID NO:1, and sequence B is at about amino acid 429 to 552 of SEQ ID NO:1. Region C is located from about amino acid 703 to amino acid 726 of SEQ ID NO:1. A "mutation" in SEQ ID NO:1 refers to a deletion, insertion, mutation or substitution of one or more amino acids. Stable HIF-1alpha can be composed of a mutation or deletion in both regions A and B. Alternatively, stable HIF-1alpha can be composed of a deletion in region C. For example, regions A and B can be deleted, regions A and B can be mutated, or region A can be mutated and region B can be deleted, region A can be deleted and region B can be mutated, or region C can be mutated, or region C can be deleted. In one nonlimiting example, stable HIF-1alpha is composed of a deletion of amino acid 392 to amino acid 520 of SEQ ID NO:1. In another nonlimiting example, stable HIF-1alpha is composed of a deletion of amino acid 392 to 428 of SEQ ID NO:1, combined with point mutation of either amino acid 551 or 552, or combined with point mutation of both amino acid 551 and 552. The point mutation(s) can be combined with a deletion of amino acids 392 to amino acid 428 of SEQ ID NO:1, or the point mutation(s) can be combined with a deletion of amino acid 392 to any amino acid between amino acid 429 and amino acid 550, inclusive, of SEQ ID NO:1.

In yet another nonlimiting example, stable HIF-1alpha is composed of a deletion of amino acid 704 to amino acid 826 of SEQ ID NO:1. This deletion eliminates the transactivation domain (amino acid 786 to amino acid 826), and thus can result in a loss of biological activity. In one embodiment, stable HIF-1alpha can be formed by deletion of amino acid 704 to amino acid 826 of SEQ ID NO:1, with the addition of a heterologous transactivation domain following amino acid 704. The "heterologous" transactivation domain is a transactivation domain derived from a polypeptide other than HIF-1I. In one embodiment, the activity of the heterologous transactivation domain is not affected by oxygen concentration. In one nonlimiting example, the heterologous transactivation domain is from the herpes simplex virus (HSVC) VP16 protein (amino acids 413–490). In this embodiment, deletion of amino acid 391 to 704 is combined with a deletion of amino acid 704 to amino acid 826. The transactivation domain from the HSV VP16 protein is then fused to amino acids 1 to 390 of the HIF-1alpha polypeptide. In yet another embodiment, a transactivation domain from HIF-1alpha (amino acids 786–826) is fused to amino acids 1–390 (Jiang et al., 1997). Additional combinations of the regions identified to be significant to the formation of sHIF1alpha mutein will readily be apparent to one of skill in the art.

A stable HIF-1alpha is an HIF-1alpha polypeptide which has an increased half-life as compared to wild-type HIF-1alpha under nonhypoxic conditions. In one embodiment, in a given cell, sHIF-1alpha has the same half-life under hypoxic or nonhypoxic conditions and is present at the same concentration in cells exposed to nonhypoxic conditions as in cells exposed to hypoxic conditions. Hypoxia is a condition where the oxygen demand in a tissue exceeds the supply of oxygen in that tissue. The terms "hypoxic" and "non-hypoxic" are understood to be relative terms with respect to oxygen concentration typically observed in a particular tissue.

The ability of wild-type HIF-1alpha to activate transcription is regulated by oxygen concentration independent of the effect of oxygen on HIF-1alpha protein stability (Jiang et al., 1997, supra). The region of sHIF-1alpha located from amino acid 576–785 is a negative regulatory domain that, when deleted, results in increased transcription under nonhypoxic conditions (Jiang et al., *J. Biol. Chem.* 272:19253, 1997, herein incorporated by reference). Thus, without being bound by theory, deletion of one or more amino acids in this sequence, such that the amino acid is replaced by a bond, results in a higher transcriptional activity, independent of the half life of the protein. Thus, deletion of amino acids 576–785 of HIF-1alpha can be combined with deletion of amino acids 392–428, and point mutation of amino acid 551 from a serine to a glycine, and point mutation of amino acid 552 from a threonine to an alanine, to yield a stable HIF-1alpha polypeptide. Deletion of amino acid 576 to amino acid 785 of HIF-1alpha can also be combined with deletion of amino acids 392 to 520 to yield a stable HIF- 1alpha polypeptide. Alternatively, deletion of amino acid 576 to amino acid 785 of HIF-1alpha can be combined to deletion of amino acid 704 to amino acid 826 (resulting in deletion of amino acid 576 to 826 of HIF-1alpha ) to yield a stable HIF-1alpha polypeptide. Such combinations will readily be apparent to one of ordinary skill in the art.

The term "substantially pure" as used herein refers to HIF-1alpha which is substantially free of other proteins, lipids, carbohydrates or other materials with which it is naturally associated. One skilled in the art can purify HIF-1alpha using standard techniques for protein purification, such as DNA affinity chromatography (e.g., Wang, G. L., and Semenza, J., *J. Biol. Chem.* 270:1230–1237, 1995) and immunoprecipitation (e.g., Jiang, B. H., et al., *J. Biol. Chem.* 271:17771–17778, 1996). The substantially pure polypeptide will yield a single band on a nonreducing polyacrylamide gel. The purity of the HIF-1alpha polypeptide can also be determined by amino-terminal amino acid sequence analysis. HIF-1alpha protein includes functional fragments of the polypeptide, as long as the activity and the stability in nonhypoxic conditions of sHIF-1alpha remains. Smaller peptides containing the biological activity of sHIF-1alpha are thus included in the invention.

The invention provides polynucleotide sequences encoding sHIF-1alpha polypeptide having a sequence as set forth in SEQ ID NO:1, wherein amino acids 392 to 428 are deleted therefrom, amino acid 551 is changed from a serine to any other amino acid, and amino acid 552 is changed from a threonine to any other amino acid. These polynucleotides include DNA, cDNA, and RNA sequences which encode sHIF-1alpha. It is also understood that all polynucleotides encoding all or a portion of sHIF-1alpha are also included herein, as long as they encode a polypeptide with HIF-1alpha activity which is stable under hypoxic and nonhypoxic conditions. Such polynucleotides include naturally occurring, synthetic, and intentionally manipulated polynucleotides. For example, sHIF-1alpha polynucleotide may be subjected to site-directed mutagenesis. The polynucleotide sequence for sHIF-1alpha also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of HIF-1alpha polypeptide is encoded by the nucleotide sequence is functionally unchanged.

Minor modifications of the sHIF-1alpha primary amino acid sequence may result in proteins which are stable under nonhypoxic conditions and have substantially equivalent activity as compared to the sHIF-1alpha polypeptide described herein. These minor modifications include the minor differences found in the sequence of HIF-1alpha polypeptide isolated from different species (e.g., human, mouse, and rat HIF-1alpha polypeptide). Such proteins include those as defined by the term "having essentially the amino acid sequence" of the sHIF-1alpha of the invention. Such modifications may be deliberate, as by site-directed mutagenesis, or may be spontaneous, as those found in different species. All of the polypeptides produced by these modifications are included herein as long as the biological activity of sHIF-1alpha still exists, and the polypeptide is stable under nonhypoxic conditions as compared to wild-type HIF-1alpha. Further, deletions of one or more amino acids can also result in modification of the structure of the resultant molecule without significantly altering its biological activity. This can lead to the development of a smaller active molecule which would have broader utility. For example, one can remove amino or carboxy terminal amino acids which are not required for sHIF-1alpha biological activity.

Specifically disclosed herein is a DNA sequence encoding the human sHIF-1alpha mutein. The invention provides polynucleotide sequences encoding stable HIF-1alpha mutein having a sequence as set forth in SEQ ID NO:1, wherein amino acids 392 to 428 are deleted therefrom, amino acid 551 is changed from a serine to any other amino acid, and amino acid 552 is changed from a threonine to any other amino acid. The wild type HIF-1alpha contains an open reading frame encoding a polypeptide 826 amino acids in length. When amino acid 551 (serine) of SEQ ID NO:1 is replaced by another amino acid, such as an glycine, or amino acid 552 (threonine) of SEQ ID NO:1 is replaced by another amino acid, such as alanine, and one or more of amino acid 392 to amino acid 429 of SEQ ID NO:1 is replaced by a bond, the polynucleotide will encode a polypeptide that is decreased in length by a corresponding number of amino acids.

In another embodiment, the invention provides polynucleotides encoding sHIF-1alpha as well as nucleic acid sequences complementary to polynucleotides encoding sHIF-1alpha. The term polynucleotide or nucleic acid sequence refers to a polymeric form of nucleotides at least 10 bases in length. By isolated polynucleotide is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double stranded forms of DNA.

A complementary sequence may include an antisense nucleotide. When the sequence is RNA, the deoxynucleotides A, G, C, and T in the polynucleotide encoding sHIF-1alpha are replaced by ribonucleotides A, G, C, and U, respectively, Also included in the invention are fragments of the above-identified nucleic acid sequences that are at least 15 bases in length, which is sufficient to permit the fragment to selectively hybridize to nucleic acid that encodes sHIF-1alpha, but not SEQ ID NO:1 under physiological conditions. Specifically, the fragments should selectively hybridize to nucleic acid encoding sHIF-1alpha polypeptide. The term "selectively hybridize" refers to hybridization under moderately or highly stringent conditions which excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.% SDS at about 42/C (moderate stringency conditions); and 0.1×SSC at about 68/C (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

When using an sHIF-1alpha specific probe, it may be necessary to amplify the nucleic acid prior to binding with an sHIF-1alpha specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

The sHIF-1alpha polynucleotide of the invention can be derived from a mammalian organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequences must be known. The DNA sequence encoding the protein can be deduced from the genetic code, however, the degeneracy of the code must be taken into account. In a preferred embodiment, the probe can delineate between sHIF-1alpha and wild-type HIF-1alpha.

It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid nonspecific binding, it is possible, for example, to allow the autoradiographic visualization of a specific cDNA clone by the hybridization of the target DNA to that single probe in the mixture which is its complete complement (Sambrook et al., *Molecular Cloning: A Laboratory Manual,* 2nd Ed.; Cold Spring Harbor Laboratory Press, Plainview, N.Y., 1998).

The development of specific DNA sequences encoding sHIF-1alpha can also be obtained by site-directed mutagenesis of a nucleic acid sequence encoding SEQ ID NO:1 or chemical manufacture of a DNA sequence to provide the necessary codons for the polypeptide of interest. The synthesis of DNA sequences is frequently the method of choice when the entire sequence of amino acid residues of the desired polypeptide product is known.

A cDNA expression library, such as in phage lambda gt11, can be screened indirectly for sHIF-1alpha peptides having at least one epitope, using antibodies specific for sHIF-1alpha. Such antibodies can be either polyclonally or monoclonally derived and used to detect expression product indicative of the presence of sHIF-1alpha cDNA DNA sequences encoding sHIF-1alpha can be expressed in vitro by DNA transfer into a suitable host cell. "Host cells" are cells in which a vector can be propagated and its DNA expressed. Host cells include both prokaryotic and eukaryotic cells. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

"Modified" versions of the specific sHIF-1alpha can be engineered to further enhance stability, biological activity, production, purification, or yield of the expressed product. For example, the expression of a fusion protein or a cleavable fusion protein comprising the sHIF-1alpha and a heterologous protein can be engineered. Such a fusion protein can be readily isolated by affinity chromatography, e.g., by immobilization on a column specific for the heterologous protein. Where a cleavage site is engineered between the HIF-1alpha moiety and the heterologous protein, the HIF-1alpha polypeptide can be released from the chromatographic column by treatment with an appropriate enzyme or agent that digests at the cleavage site (Booth et al., *Immunol. Lett.* 19:65–708, 1988; Gardella et al., *J. Biol. Chem.* 265:15854–15859, 1990).

The invention provides an isolated nucleic acid sequence encoding a fusion protein. The fusion protein is encoded by a nucleotide sequence encoding a DNA binding domain and a dimerization domain of a hypoxia inducible factor, preferably HIF-1alpha; and a nucleotide sequence encoding a transcriptional activation domain. This "chimeric" transactivator is useful for affecting gene expression of target genes, such as VEGF, and neovascularization of ischemic tissue. The nucleotide sequence encoding a DNA binding domain and a dimerization domain of a hypoxia inducible factor is useful for providing constitutive activation of genes regardless of the oxygen concentration in the surrounding environment. A chimeric transactivator of the invention provides for the specific activation of expression of hypoxia-inducible genes containing hypoxia responsive elements (HREs), thereby achieving high levels of gene expression. The HREs each contain a binding site for HIF-1, which is recognized by the chimeric transactivator due to the presence of the HIF-1alpha dimerization and DNA binding domains. Invention chimeric transactivating proteins function in vertebrate cells and may include naturally occurring transcriptional transactivating proteins or domains of proteins from eukaryotic cells including vertebrate cells, viral transactivating proteins, or any synthetic amino acid sequence that is able to stimulate transcription from a vertebrate promoter.

A transactivation domain of the chimeric transactivator is derived from transactivating proteins, including but not limited to HSV VP 16, a heat shock factor, p53, fos, v-jun, factor EF-C, HIV tat, HPV E2, Ad E1A, Sp1, AP1, CTF/ NF1, E2F1, HAP1, HAP2, MCM1, PHO2, GAL4, GCN4, and GAL11, and NFkB and other heterologous proteins that have such a transactivating domain. One of skill in the art will recognize that a transcriptional activation domain for use in a composition of the invention can be from a naturally occurring protein or can be synthetic, e.g., based on a sequence not contained in a naturally occurring protein. Identification of a transactivation domain can be determined by operably linking a desired domain from a protein with an appropriate sequence and assaying for expression of a reporter sequence.

A recombinant nucleic acid construct encoding a chimeric transactivator protein of the invention may be placed under the control of or "operatively linked to" a suitable promoter and/or other expression control regulatory sequences. It may be desirable for the transactivator protein to be placed under the control of a constitutively active promoter sequence, although the transactivator protein may also be placed under the control of an inducible promoter, such as the metallothionein promoter or a tissue specific promoter. An inducible promoter allows for controlled increase or decrease of expression of a particular gene, while constitutive expression allows for continual expression of a gene, for example, for producing a gene product in culture, or in a transgenic animal. Other promoter sequences that are useful include, but are not limited to, the SV40 early promoter region; RSV or other retroviral LTRs; herpes thymidine kinase promoter, human cytomegalovinis (CMV) immediate early promoter/enhancer. Other promoters that have been used for this purpose include the elastase 1 gene control region; insulin gene control region; immunoglobulin gene control region; mouse mammary tumor virus control region; albumin gene control region; alpha-fetoprotein gene control region; alpha 1-antitrypsin gene control region and beta-globin gene control region.

The nucleic acid sequence encoding the DNA binding domain and dimerization domain of HIF-1alpha and the heterologous transactivation domain are operably linked so that the structural and functional activities of each region is retained (i.e., DNA binding, dimerization and transactivating activity). FIGS. 2 and 3 provide results of various deletions in HIF-1alpha and the effects on regulation of gene expression. Based on the results shown in the figures and in U.S. Pat. No. 5,882,914, the invention chimeric transactivator may include a DNA binding and dimerization region which encodes, for example, HIF-1alpha amino acids 1–703of SEQ ID NO: 1; amino acids 1–681 of SEQ ID NO: 1; amino acids 1–608 of SEQ ID NO: 1; or amino acids 1–391 of SEQ ID NO: 1.

The invention also includes expression vectors containing a nucleic acid sequence encoding a chimeric transactivator as described herein. Vectors include, adenovirus, AAV, lentivirus, herpes virus, vaccinia virus, baculovirus, retrovirus, bacteriophage, cosmids, plasmids, phosmids, fungal vectors and other vectors known in the art that are used for expression in eukaryotic and prokaryotic host cells, and may be used in vivo for gene therapy or in vitro in cell culture, for example.

Stable HIF-1alpha proteins of the invention also include, but are not limited to, HIF-1alpha amino acid residues 1–391 and 521–826 of SEQ ID NO:1; amino acid residues 1–391 and 549–826 of SEQ ID NO:1; amino acid residues 1–391 and 576–826 of SEQ ID NO:1; amino acid residues 1–391 and 429–826 of SEQ ID NO:1, wherein 551 is no longer serine and 552 is not threonine; amino acid residues 1–391 and 469–826 of SEQ ID NO:1, wherein 551 is no longer serine and 552 is not threonine; amino acid residues 1–391 and 494–826 of SEQ ID NO:1, wherein 551 is no longer serine and 552 is not threonine; amino acid residues 1–391 and 508–826 of SEQ ID NO:1, wherein 551 is no longer serine and 552 is not threonine; amino acid residues 1–391 and 512–826 of SEQ ID NO:1, wherein 551 is no longer serine and 552 is not threonine; and amino acid residues 1–391 and 517–826 of SEQ ID NO:1, wherein 551 is no longer serine and 552 is not threonine. When 551 serine is changed, for example, amino acid residue 551 may be glycine. Further, when 552 threonine is changed, amino acid residue 552 may be alanine. In addition to these polypeptides, the invention includes nucleic acid sequences encoding such polypeptides and expression vectors containing such nucleic acid sequences.

It should be understood that one of skill in the art can manipulate the amino acid or nucleic acid sequences provided herein by deleting or adding amino acid residues or nucleotides, respectively, as long as the activity ascribed to the sequences is retained, e.g., constitutive transactivation or stable HIF-1alpha properties as described herein. One of skill in the art could use the teachings herein to assay for such activities (see the Examples).

In the present invention, the sHIF-1alpha polynucleotide sequences may be inserted into an expression vector. The term "expression vector" refers to a plasmid, virus or other vehicle known in the art that has been manipulated by insertion or incorporation of the sHIF-1alpha genetic sequences. Polynucleotide sequence which encode sHIF-1alpha can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, as start codon (i.e., ATG) in front of a protein-encoding gene, splicing signal for introns, maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., *Methods in Enzymology* 153:516–544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein or elongation factor-1alpha promoter) or from mammalian viruses (e.g., the retrovirus long terminal repeat; the adenovirus late promoter; the vaccinia virus 7.5K promoter; the cytomegalovirus promoter) may be used. Promoters produced by recombinant DNA or synthetic techniques may also be used to provide for transcription of the nucleic acid sequences of the invention.

In the present invention, the polynucleotide encoding sHIF-1alpha may be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., CMV, T7, metallothionein I, or polyhedrin promoters).

Mammalian expression systems which utilize recombinant viruses or viral elements to direct expression may be engineered. For example, when using adenovirus expression vectors, the sHIF-1alpha coding sequence may be ligated to an adenovirus transcription/translation control complex, e.g., the late promoter and tripartite leader sequence or a heterologous (e.g., CMV) promoter cloned into a replication-deficient adenovirus (Armentano, D., et al., Hum. Gene Ther. 6:1343–1353, 1995; Hehir, K. M., et al., J. Virol. 70:8459–8467, 1996). Alternatively, the vaccinia virus 7.5K promoter may be used. (e.g., see, Mackett et al., *Proc. Natl. Acad. Sci. USA* 79:7415–7419, 1982; Mackett et al., *J. Virol.* 49:857–864, 1984; Panicali et al., *Proc. Natl. Acad. Sci. USA* 79:4927–4931, 1982). Vectors based on bovine papilloma virus have the ability to replicate as extrachromosomal elements (Sarver, et al., *Mol. Cell. Biol.* 1:486, 1981). Shortly after entry of this nucleic acid into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the sHIF-1alpha gene in host cells (Cone & Mulligan, *Proc. Natl. Acad. Sci. USA* 81:6349–6353, 1984). High level expression may also be achieved using inducible promoters, including, but not limited to, the metallothionein IIA promoter and heat shock promoters.

Depending upon the vector utilized, polynucleotide sequences encoding sHIF-1alpha can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

For long-term, high-yield production of recombinant proteins, stable expression is preferred. Rather than using expression vectors which contain viral origins of replication, host cells can be transformed with sHIF-1alpha cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign nucleic acid, engineered cells may be allowed to grow for 1–2 days in an enriched media, and then are switched to a selective media. A number of selection systems may be used, including, but not limited to the herpes simplex virus thymidine kinase gene (Wigler, et al., *Cell* 11:223, 1977), hypoxanthine-guanine phosphoribosyltransferase gene (Szybalska & Szybalski, *Proc. Natl. Acad. Sci. USA* 48:2026, 1962), and the adenine phosphoribosyltransferase (Lowy, et al., *Cell* 22:817, 1980) genes can be employed in tk–, hgprt– or aprt– cells respectively. Additionally, antimetabolite resistance can be used as the basis of selection for dhfr, which confers resistance to methotrexate (Wigler, et al., *Natl. Acad. Sci. USA* 17:3567, 1980; O'Hare, et al., *Proc. Natl. Acad. Sci. USA* 78:1527, 1981); the gpt gene, which confers resistance to mycophenolic acid (Mulligan & Berg, *Proc. Natl. Acad. Sci. USA* 78:2072, 1981; the neo gene, which confers resistance to the aminoglycoside G-418 (Colberre-Garapin, et al., *J. Mol. Biol.* 150:1, 1981); and the hygro gene, which confers resistance to hygromycin (Santerre, et al., *Gene* 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047, 1988); and ODC (ornithine decarboxylase) which confers resistance to the ornithine decarboxylase inhibitor, 2-(difluoromethyl)-DL-ornithine, DFMO (McConlogue L., In: *Current Communications in Molecular Biology*, Cold Spring Harbor Laboratory ed., 1987).

By "transformation" is meant a genetic change induced in a cell following incorporation of new DNA (i.e., DNA exogenous to the cell). Where the cell is a mammalian cell, the genetic change is generally achieved by introduction of the DNA into the genome of the cell (i.e., stable).

By "transformed cell" is meant a cell into which (or into an ancestor of which has been introduced, by means of recombinant DNA techniques, a DNA molecule encoding sHIF-1alpha. Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the sHIF-1alpha of the invention, and a second foreign DNA molecule encoding a selectable phenotype, such as the herpes simplex thymidine kinase gene. Another method is to use a eukaryotic viral vector, such as simian virus 40 (SV40), adenovirus, or bovine papilloma virus, to transiently infect or transform eukaryotic cells and express the protein (see for example, *Eukaryotic Viral Vectors*, Cold Spring Harbor Laboratory, Gluzman, ed., 1982).

Isolation and purification of microbial expressed polypeptide, or fragments thereof, provided by the invention, may be carried out by conventional means including preparative chromatography and immunological separations involving monoclonal or polyclonal antibodies.

The HIF-1alpha polypeptides of the invention can also be used to produce antibodies which are immunoreactive or selectively bind to epitopes of the sHIF-1alpha polypeptides. An antibody which "selectively binds" to sHIF-1alpha is an antibody that binds sHIF-1alpha with a higher affinity the antibody binds to wild-type HIF-1alpha. Thus, antibodies of the invention can be used to distinguish the presence of sHIF-1alpha mutein from wild-type HIF-1alpha polypeptide. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler et al. *Nature* 256:495, 1975; *Current Protocols in Molecular Biology*, Ausubel et al., ed., 1989).

The term "antibody" as used in this invention includes intact molecules as well as fragments thereof, such as Fab, F(ab')2, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. See, for example, Harlow and Lane, *Antibodies: A Laboratory Manual*, Cold Spring Harbor Laboratory, New York, 1988, incorporated herein by reference.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which selectively bind to the sHIF-1alpha polypeptide of the invention, can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies. See, for example, Coligan et al., Unit 9, *Current Protocols in Immunology*, Wiley Interscience, 1994, herein specifically incorporated by reference.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

For purposes of the invention, an antibody or nucleic acid probe specific for sHIF-1alpha may be used to detect sHIF-1alpha polypeptide or polynucleotide in biological fluids, cultured cells or tissues. The antibody reactive with sHIF-1alpha or the nucleic acid probe is preferably labeled with a compound which allows detection of binding to sHIF-1alpha. Any specimen containing a detectable amount of antigen or polynucleotide can be used.

The invention provides methods for treatment of HIF-1-mediated disorders, including hypoxia- or ischemia-related tissue damage, which are improved or ameliorated by modulation of HIF-1 expression or activity. The term "modulate" envisions the induction or augmentation of HIF-1 expression when appropriate. The term "ameliorate" denotes a lessening of the detrimental effect of the associated disease in the subject receiving therapy. Where expression or augmentation of expression of HIF-1 is desirable, the method of the treatment includes administration of substantially purified sHIF-1alpha polypeptide or polynucleotide encoding the same.

According to the method of the invention, substantially purified sHIF-1alpha mutein or the polynucleotide sequence encoding sHIF-1alpha in an appropriate vector is introduced into a human patient for the treatment or prevention of hypoxia/ischemia-related tissue damage. Non-limiting examples include patients with coronary, cerebral, or peripheral arterial disease and patients with one or more non-healing wounds.

The relevant clinical conditions treated by the methods and compositions of the invention include ischemia due to disease of the cerebral, coronary, or peripheral circulation. One therapeutic goal is to promote angiogenesis in the ischemic tissue by overexpression of sHIF-1alpha, which would dimerize with endogenous HIF-1beta, bind to specific DNA sequences, and activate transcription of hypoxia-inducible genes relevant to angiogenesis, such as, but not limited to, the gene encoding vascular endothelial growth factor (VEGF), a known HIF-1 target gene (J. A. Forsythe et al., *Mol Cell Biol* 16:4604,1996; N. V. Iyer et al., Genes Dev 12: 149, 1998). The rationale for using HIF-1alpha is that because it is a transcription factor that controls the expression of multiple genes involved in angiogenesis it will give a superior clinical outcome compared to treatment with a single angiogenic factor such as VEGF. However, the method of delivery of DNA to the tissue site is in no way affected by the identity of the particular gene being delivered. Further, many patients with coronary artery disease do not have reduced myocardial blood flow or hypoxia at rest. It is only when they are active and require increased myocardial blood flow that they experience anginal symptoms resulting from myocardial ischemia. Alternatively, a narrowed coronary vessel may become completely occluded either by spasm or a clot, resulting in a myocardial infarction (heart attack). Therefore the goal of the treatment with the stable form of HIF-1alpha is to induce angiogenesis in these patients, even if there is no hypoxia at the time, in order to prevent heart attacks. Accordingly, the stable HIF-1alpha compositions of the invention provide prophylactic as well as therapeutic treatment regimens.

The present invention provides the introduction of polynucleotides encoding sHIF-1alpha for the treatment of hypoxia-related disorders, which are improved or ameliorated by expression of the HIF-1alpha polypeptide. Such therapy would achieve its therapeutic effect by introduction of the sHIF-1alpha polynucleotide into cells exposed to hypoxic conditions. HIF-1alpha is thus expressed in both the hypoxic and surrounding nonhypoxic tissues, such that it can dimerize with HIF-1beta (which is present in excess in hypoxic and nonhypoxic cells), and activate the transcription of downstream target genes. Examples of genes which can be activated by HIF-1 are vascular endothelial growth factor, glucose transporters, glycolytic enzymes, and insulin-like growth factor 2. These genes mediate important adaptive responses to hypoxia including angiogenesis and glycolysis, and prevention of cell death.

Based upon the preceding, the invention provides a method for increasing expression of a hypoxia inducible gene in a cell. The method includes contacting the cell with an expression vector containing a polynucleotide encoding a stable HIF-1alpha of the invention or a chimeric transactivator protein as described herein under conditions that allow expression of the nucleic acid sequence contained in the vector thereby providing for increased expression of a hypoxia inducible gene in the cell. Such genes include, for example, those encoding VEGF, glucose transporters, glycolytic enzymes, IGF-2, IGF binding proteins and the like.

The invention further provides a method for providing constitutive expression of a hypoxia inducible factor in a cell, under hypoxic or non-hypoxic conditions. The method includes contacting the cell with a nucleic acid sequence encoding a chimeric transactivator protein as described herein, or a stable HIF-1alpha as described herein, under conditions that allow expression of the nucleic acid sequence, thereby providing constitutive expression of a hypoxia inducible factor.

Further included in the invention is a method for reducing hypoxia or ischemia-related tissue damage in a subject having or at risk of having such damage. The method includes administering to the subject a therapeutically effective amount of a nucleic acid sequence encoding a chimeric transactivator protein as described herein, or a stable HIF-1alpha as described herein, in a pharmaceutically acceptable carrier, thereby reducing the tissue damage.

In another embodiment, the invention provides a method for providing prophylactic therapy for tissue in a subject in need thereof comprising administering to the subject an amount of a polypeptide encoded by a polynucleotide encoding a chimeric transactivator protein as described herein, or a stable HIF-1alpha as described herein, such that angiogenesis is induced at levels that are greater than before administration of the polypeptide, thereby providing prophylactic therapy.

Delivery of sHIF-1alpha polynucleotide can be achieved using a recombinant expression vector such as a chimeric virus or a colloidal dispersion system. Especially preferred for therapeutic delivery of sequences is the use of targeted liposomes.

Various viral vectors which can be utilized for gene therapy as taught herein include adenovirus, adeno-associated virus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a sHIF-1alpha sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the SHIF-1alpha polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to 2,PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for HIF-1 polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LW), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley et al., *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al. *Biotechniques* 6:682, 1988).

The composition of the liposome is usually a combination of phospholipids, particularly high-phase-transition-temperature phospholipids, usually in combination with sterols, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidyl-glycerol, phosphatidylcholine, phosphatidylserine, phosphatidylethanolamine, sphingolipids, cerebrosides, and gangliosides. Particularly useful are d-iacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

sHIF-1alpha polypeptide can be used in therapeutic administration. For such administration the polypeptide must be sterile. Sterility is readily accomplished by sterile filtration through (e.g., 0.2 micron) membranes. The compound of the invention ordinarily will be stored as unit or multidose containers, for example, sealed ampules or vials, as an aqueous solution, as it is highly stable to thermal and oxidative denaturation. Lyophilized formulations for reconstitution are also acceptable. The polypeptide will be administered as a pharmaceutical composition (see below).

The invention also describes a method of treating a subject having a hypoxia related disorder by administering to the subject a therapeutically-effective amount of cells expressing sHIF-1alpha. "Therapeutically-effective" as used herein, refers to that amount of cells that is of sufficient quantity to alleviate a symptom of the disease or to ameliorate the hypoxia-related disorder. The effective amount results in expression of biologically active stable HIF-1alpha for a period of time such that one or more symptoms of the disease/disorder is alleviated. Such methods are useful to increase or sustain the expression of HIF-1alpha and/or hypoxia-inducible genes in tissues under hypoxic or non-hypoxic conditions.

In some preferred embodiments of the methods of the invention described above, the sHIF-1alpha is administered locally (e.g., interlesionally) and/or systemically. The term "local administration" refers to delivery to a defined area or region of the body, such as for non-healing wounds, while the term "systemic administration is meant to encompass delivery to the subject by oral route, or by intramuscular, intravenous, intraarterial, subcutaneous, or intraperitoneal injection.

The term "pharmaceutically acceptable" means a non-toxic material that does not interfere with the effectiveness of the biological activity of the active ingredient(s). The term "physiologically acceptable" refers to a non-toxic material that is compatible with a biological system such as a cell, cell culture, tissue, or organism.

The sHIF-1alpha compositions of the invention may be used as part of a pharmaceutical composition when combined with a physiologically and/or pharmaceutically acceptable carrier. The characteristics of the carrier will depend on the route of administration. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which enhance expression or which aid in stimulating angiogenesis. For example, sHIF-1alpha in combination with VEGF may be used in the pharmaceutical compositions of the invention.

The pharmaceutical composition of the invention may be in the form of a liposome in which the sHIF-1alpha compositions of the invention are combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. One particularly useful lipid carrier is lipofectin. Preparation of such liposomal formulations is within the level of skill in the art, as disclosed, for example, in U.S. Pat. Nos. 4,235,871; 4,501,728; 4,837,028; and 4,737,323. The pharmaceutical composition of the invention may further include compounds such as cyclodextrins and the like which enhance delivery of nucleic acid molecules into cells, or slow release polymers.

When a therapeutically effective amount of composition of the invention is administered by intravenous, subcutaneous, intramuscular, intraarterial, intraocular, or intraperitoneal injection, the composition will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, subcutaneous, intramuscular, intraperitoneal, or intraocular injection should contain, in addition to the sHIF-1alpha composition, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of sHIF-1alpha composition, in the pharmaceutical composition of the present invention will depend upon the nature and severity of the condition being treated, and on the nature of prior treatments which the patent has undergone. Ultimately, the attending physician will decide the amount of sHIF-1alpha composition, with which to treat each individual patient. Initially, the attending physician will administer low doses of the sHIF-1alpha composition, and observe the patient's response. Larger doses of sHIF-1alpha composition, may be administered until the optimal therapeutic effect is obtained for the patient, and at that point the dosage is not increased further. It is contemplated that the various pharmaceutical compositions used to practice the method of the present invention should contain about 10 ug to about 20 mg of sHIF-1alpha composition,per kg body or organ weight.

The duration of intravenous therapy using the pharmaceutical composition of the present invention will vary, depending on the severity of the disease being treated and the condition and potential idiosyncratic response of each individual patient. Ultimately the attending physician will decide on the appropriate duration of intravenous therapy using the pharmaceutical composition of the present invention.

Transduction of the cell is performed in vitro, generally with isolated cell populations or cell lines. The cells may be xenogeneic, allogeneic, syngeneic or autologous, preferably autologous, in order to reduce adverse immune responses. The cells may be administered in any physiologically acceptable medium, normally intravascularly, although they may also be introduced into tissue surrounding a vessel or other convenient site, where the cells may find an appropriate site for expansion and differentiation. "Ameliorate" refers to lessening or lowering the disease's or disorder's detrimental effect in the patient receiving the therapy.

Any of the transplantation or implantation procedures known in the art can be utilized. For example, the selected cells or cells of interest can be surgically implanted into the recipient or subject. Transplantation or implantation is typically by simple injection through a hypodermic needle having a bore diameter sufficient to permit passage of a suspension of cells therethrough without damaging the cells or tissue coating. For implantation, the typically encapsulated or coated cells are formulated as pharmaceutical compositions together with a pharmaceutically-acceptable carrier. Such compositions contain a sufficient number of coated transplant cells which can be injected into, or administered through a laparoscope to, a subject. Usually, at least about $1 \times 10^4$ to $1 \times 10^5$ cells will be administered, preferably $1 \times 10^6$ or more. The cells may be frozen at liquid nitrogen temperatures and stored for long periods of time, being capable of use on thawing. Once thawed, the cells may be expanded. Further, the cells can be administered in an encapsulated form or non-encapsulated form. Preferably the cells are encapsulated.

While not required, it may be desirable to administer an immunosuppressive agent to a recipient of the cells, prior to, simultaneous with, and/or after transplantation. In particular, an immunosuppressive agent can be utilized with xenogeneic or allogeneic cells expressing sHIF-1alpha. An agent such as Cyclosporine A (CsA) is preferable, however other immune suppressive agents can be used, such as rapamycin, desoxyspergualine, FK506 and like. These agents are administered to cause an immunosuppressive effect in the subject, such that the transplanted cells are not rejected by that subject's immune system. Typically, the immunosuppressive agent is administered continuously through-out the transplant treatment typically over a period of days or weeks; for example, CsA treatment ranges from about 2 to about 20 days at a dosage range of about 5 to 40 mg per kilogram of body weight per day. The agent can be administered by a variety of means, including parenteral, subcutaneous, intrapulmonary, oral, intranasal administration and the like. Preferably, dosing is given by oral administration.

The cells expressing HIF-1alpha also can be encapsulated prior to transplantation. Although the cells are typically microencapsulated, they can be encased in various types of hollow fibers or in a block of encapsulating material. A variety of microencapsulation methods and compositions are known in the art. A number of microencapsulation methods for use in transplant therapy have focused on the use of alginate polymers or agarose to supply the encapsulation compositions. Alginates are linear polymers of mannuronic and guluronic acid residues which are arranged in blocks of several adjacent guluronic acid residues forming guluronate blocks and block of adjacent mannuronic acid residues forming mannuronate blocks, interspersed with mixed, or heterogenous blocks of alternating guluronic and mannuronic acid residues. Generally, monovalent cation alginate salts are soluble, e.g., Na-alginate.

Divalent cations, such as $Ca^{++}$, $Ba^{++}$ or $Sr^{++}$, tend to interact with guluronate, and the cooperative binding of these cations within the guluronate blocks provides the primary intramolecular crosslinking responsible for formation of stable ion-paired alginate gels. Alginate encapsulation methods generally take advantage of the gelling of alginate in the presence of these divalent cation solutions. In particular, these methods involve the suspension of the material to be encapsulated, in a solution of monovalent cation alginate salt, e.g., sodium. Droplets of the solution are then generated in air and collected in a solution of divalent cations, e.g., $CaCl_2$. The divalent cations interact with the alginate at the phase transition between the droplet and the divalent cation solution resulting in the formation of a stable alginate gel matrix being formed. Generation of alginate droplets has previously been carried out by a number of methods. For example, droplets have been generated by extrusion of alginate through a tube by gravitational flow, into a solution of divalent cations. Similarly, electrostatic droplet generators which rely on the generation of an electrostatic differential between the alginate solution and the divalent cation solution have been described. The electrostatic differential results in the alginate solution being drawn through a tube, into the solution of divalent cations. Methods have been described wherein droplets are generated from a stream of the alginate solution using a laminar air flow extrusion device. Specifically, this device comprises a capillary tube within an outer sleeve. Air is driven through the outer sleeve and the polymer solution is flow-regulated through the inner tube. The air flow from the outer sleeve breaks up the fluid flowing from the capillary tube into small droplets (see U.S. Pat. No. 5,286,495). For a general discussion of droplet generation in encapsulation processes, see, e.g., M. F. A. Goosen, Fundamentals of Animal Cell Encapsulation and Immobilization, Ch. 6, pp. 114–142 (CRC Press, 1993).

Attempts to transplant organ tissues into genetically dissimilar hosts without immunosuppression are generally defeated by the immune system of the host. Accordingly, attempts have been made to provide other effective protective barrier coatings, e.g., by microencapsulation, to isolate the transplant tissues from the host immune system. Successful cell or tissue transplants generally require a coating that will prevent their destruction by a host's immune system, prevent fibrosis, and will be permeable to and allow a free diffusion of the nutrients to the coated transplant and removal of the secretory and waste products from the coated transplant. Viable tissue and cells have been successfully immobilized in alginate capsules coated with polylysine (see above and *J. Pharm. Sci.* 70:351–354, 1981). The development of transplants encapsulated in calcium alginate capsules reacted with polylysine is also described, for example, in U.S. Pat. Nos. 4,673,566, 4,689,293, 4,789,550, 4,806,355, and 4,789,550. U.S. Pat. No. 4,744,933 describes encapsulating solutions containing biologically active materials in a membrane of inter-reacted alginate and polyamino acid. U.S. Pat. No. 4,696,286 reports a method for coating transplants suitable for transplantation into genetically dissimilar individuals. The method involves coating the transplant with a surface conforming bonding bridge of a multifunctional material that binds chemically to a surface component of the transplant, which is enveloped in a semipermeable, biologically compatible layer of a polymer that binds chemically to the bonding bridge layer. A method for introducing a second alginate gel coating to cells already coated with polylysine alginate is described in U.S. Pat. No. 5,227,298. Both the first and second coating of this method require stabilization by polylysine.

Encapsulation methods applied to make these materials have comprised a procedure for forming droplets of the encapsulating medium and the biological material and a procedure for solidifying the encapsulating medium. Agarose encapsulated materials have been formed by chilling an emulsion of agarose droplets containing biological materials as shown by Nilsson, et al., *Nature* 302:629–630 (1983) and Nilsson, et al., *Eur. J. Appl. Microbiol. B-iotechnol.* 17:319–326 (1983). Injection of droplets of polymer containing biological materials into a body of coolant such as concurrently liquid stream has been reported by Gin, et al., *J. Microencapsulation* 4:329–242 (1987).

This invention involves administering to a subject a therapeutically effective dose of a pharmaceutical composition containing the compositions of the present invention and a pharmaceutically acceptable carrier. "Administering" the pharmaceutical composition of the present invention may be accomplished by any means known to the skilled artisan.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, orally, intravenously, or by another parenteral route, or as implants, or even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science,* 249:1527–1533, 1990, which is incorporated herein by reference.

For delivery of sHIF-1alpha mutein, the formulations are prepared by contacting sHIF-1alpha mutein uniformly and intimately with liquid carriers or finely divided solid carriers or both, and then, if necessary, shaping the product into the desired formulation. Preferably the carrier is a parenteral carrier, more preferably a solution that is isotonic with the blood of the recipient. Examples of such carrier vehicles include water, saline, Ringer's solution, dextrose solution, and 5% human serum albumin. Nonaqueous vehicles such as fixed oils and ethyl oleate are also useful herein, as well as liposomes. Generally, the carrier can contain minor amounts of additives such as substances that enhance isotonicity and chemical stability, e.g., buffers and preservatives, as well as low molecular weight (less than about 10 residues) polypeptides, proteins, amino acids, carbohydrates including glucose or dextrans, chelating agents such as EDTA, or other excipients.

The composition herein is also suitably administered by sustained release systems. Suitable examples of sustained release compositions include semipermeable polymer matrices in the form of shaped articles, e.g., films, microcapsules, or microspheres. Sustained release matrices include, for example, polyactides (U.S. Pat. No. 3,773,919), copolymers of L-glutamic acid and -ethyl-L-glutamate (Sidman et al., *Biopolymers* 22:547–556, 1983), or poly-D-(-)-3-hydroxybutyric acid (EP 133,988). Sustained release compositions also include one or more liposomally entrapped compounds of formula I. Such compositions are prepared by methods known per se, e.g., as taught by Epstein et al. *Proc. Natl. Acad. Sci. USA* 82:3688–3692, 1985. Ordinarily, the liposomes are of the small (200–800 Å) unilamellar type in which the lipid content is greater than about 30 mol % cholesterol, the selected proportion being adjusted for the optimal therapy.

The pharmaceutical compositions according to the invention may be administered locally or systemically. By "therapeutically effective dose" is meant the quantity of a compound according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman And Gilman's: The Pharmacological Bases of Therapeutics,* 8th ed., Pergamon Press, 1990; and *Remington's Pharmaceutical Sciences,* 17th ed., Mack Publishing Co., Easton, Pa., 1990; each of which is herein incorporated by reference.

Stable HIF-1alpha and chimeric transactivator compositions of the invention can also be delivered in the form of naked DNA, for example by the methods described in U.S. Pat. No. 5,589,466.

The following examples are intended to illustrate but not limit the invention. While they are typical of those that might be used, other procedures known to those skilled in the art may alternatively be used.

EXAMPLE 1

Generation of A Constitutively Expressed Form of HIF-1alpha

It has previously been shown (Jiang et al., *J. Biol. Chem* 272:19253, 1997; Pugh et al., *J. Biol. Chem.* 272:11205) that a fusion protein consisting of the GAL4 DNA binding domain fused to HIF-1alpha residues 531–826 is a constitutively expressed protein that can activate transcription of reporter genes containing GAL4 binding sites. However, these GAL4/HIF-1alpha constructs do not activate the normal target genes regulated by HIF-1. Conversely, it was shown that HIF-1alpha amino acids 1–390 are sufficient for dimerization of HIF-1alpha to HIF-1beta and binding to target DNA sequences but insufficient for optimal activation of gene transcription (Jiang, B. H., et al., J. Biol. Chem. 271:17771–17778, 1996; U.S. Pat. No. 5,882,914).

To generate a constitutively expressed form of HIF-1alpha, two series of deletion constructs were produced, one in which the deletions began at the carboxyl-terminal end of the molecule (amino acid 826) and extended towards the amino terminus, and one in which the deletions began at amino acid 392 and extended towards the carboxyl terminus.

Each of these constructs was expressed in mammalian cells under nonhypoxic (20% $O_2$) or hypoxic (1% $O_2$) conditions, and the expression of endogenous full length HIF-1alpha and transfected deleted HIF-1alpha was quantitated by immunoblot assay using affinity-purified anti-HIF-1alpha antibodies. These studies revealed that endogenous HIF-1alpha showed regulated expression (more protein expressed in cells at 1% $O_2$ than in cells at 20% $O_2$). In addition the studies showed that C-terminal deletion to amino acid 726 had no effect on the regulation of HIF-1alpha protein expression by $O_2$ concentration, whereas deletion to amino acid 703 or beyond resulted in loss of regulation (i.e., constitutive expression, see FIG. 2). Internal deletions extending from amino acid 392 through 517 had no effect on expression, whereas deletion of amino acid 392 to amino acid 521 resulted in loss of regulation (see FIG. 3). In addition, the missense mutations S551G/T552A (a serine to glycine and threonine to alanine substitution at amino acid 551 and 552, respectively) resulted in loss of regulation of the internal deletion constructs that otherwise showed regulation (ie., deletions extending from amino acid 392 to anywhere between amino acid 429 and 517). These missense mutations alone did not cause dysregulated expression of full-length HIF-1alpha (amino acids 1–826, see FIG. 3).

The results suggested that there were two regions of HIF-1alpha that were required for regulated expression, such that deletion of either region resulted in dysregulated expression (see FIG. 4). The first of these regions is region AB (amino acid 392–552). Within this internal region, two sequences (A and B) were identified that appeared functionally redundant, since the presence of either sequence was sufficient for regulation. One of these sequences (A) was identified by the 392–428 deletion and the other sequence (B) was identified by the 392–520 deletion, or the S551G/T552A point mutations. This latter result suggested that the serine and/or threonine residue was subjected to phosphorylation/dephosphorylation which could be disrupted by the 392–520 deletion. Since loss of the serine/threonine sequence mimicked hypoxia, these results suggest phosphorylation of serine 551 and/or threonine 552 under nonhypoxic conditions and dephosphorylation under hypoxic conditions. Based upon the redundancy of A and B, it is possible that a phosphatase may also bind at the A site and dephosphorylate a nearby serine or threonine reside.

Region C is defined by the different effects of deletions encompassing amino acids 704 to 826 as compared to deletions encompassing amino acids 727 to 826. Loss of region C is not redundant with the loss of region AB, thus it is likely that this region will be involved in some other function related to regulation of HIF-1alpha stability. Without being bound by theory, it is possible this region is involved in ubiquitination or proteolysis.

Figure 5:
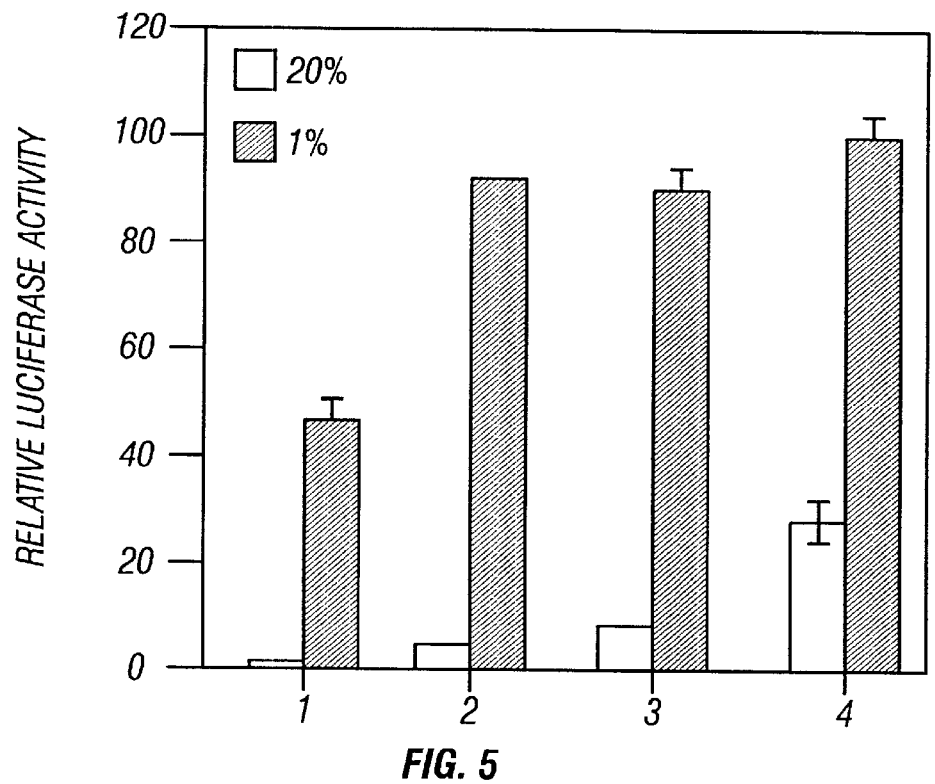
FIG. 5 is a bar graph illustrating the luciferase activity upon cotransfection of human 293 cells with a reporter gene containing a hypoxic response element (that includes a HIF-1 binding site) with expression vector pCEP4 encoding (1) no protein; (2) full-length HIF-1alpha (amino acids 1-826); (3) HIF-1alpha (1–391/429–826, deletion only); (4) HIF-1alphaDP (deletion and a serine to glycine mutation at amino acid 551 and a threonine to alanine mutation at residue 552). Reporter gene expression is shown at 1% (black bars) and 20% $O_2$ (white bars).
Figure 6:
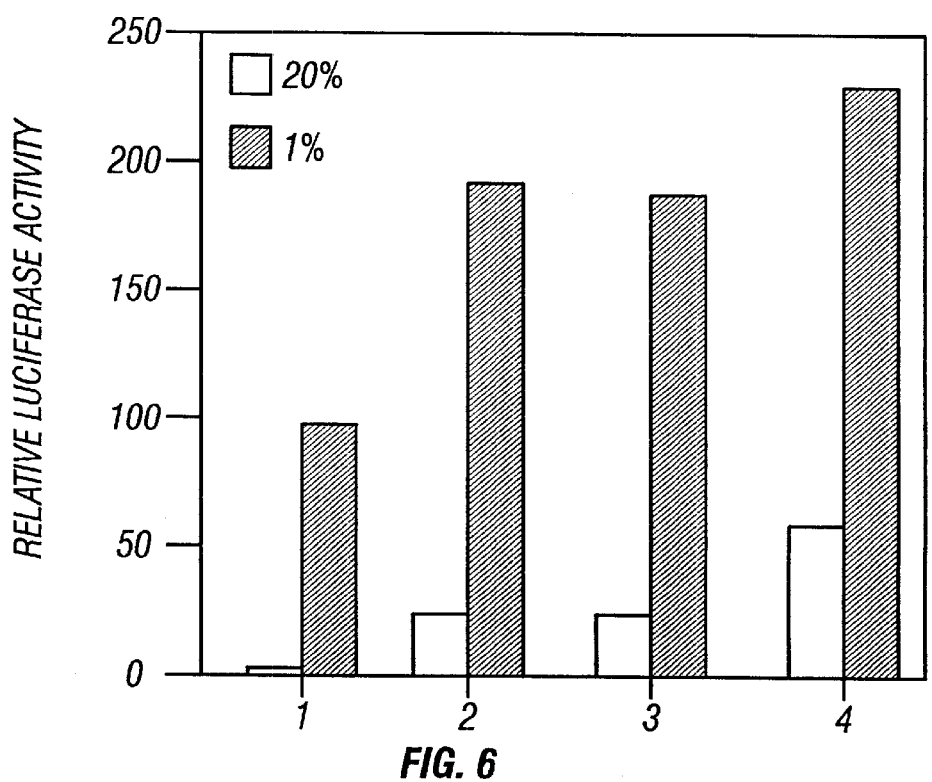
FIG. 6 is a bar graph illustrating the luciferase activity upon cotransfection of Hep3B cells with a reporter gene containing a hypoxic response element (that includes a HIF-1 binding site) and with expression vector pCEP4 encoding (1) no protein; (2) HIF-1alpha; (3) HIF-1alpha (1–391/429–826, deletion only); (4) HIF-1alphaDP (deletion and a serine to glycine mutation at amino acid 551 and a threonine to alanine mutation at residue 552). Reporter gene expression is shown at 1% (black bars) and 20% $O_2$ (white bars).

A powerful transactivation domain is located between amino acids 786 and 826. As a result, although HIF-1alpha (amino acid 1–703) is constitutively expressed, it is not as biologically active as full-length HIF-1alpha. In order to determine if sHIF-1alpha would demonstrate increased biological activity compared to full-length HIF-1alpha cotransfection experiments using the deletion/point mutant HIF-1alpha (1–391/512–826/S551G/T552A), a stable HIF-1alpha, were performed. Either 293 cells (see FIG. 5) or Hep3B cells (see FIG. 6) were cotransfected with a reporter gene containing a hypoxia response element that includes an HIF-1 binding site, and with mammalian expression vector pCEP4 (Invitrogen) encoding either (1) no protein, (2) HIF-1alpha (1–826), (3) HIF-1alpha (1–391/429–826) (deletion only), or (4) stable HIF-1alpha (HIF-1alphaDP, a form of sHIF-1alpha which contains 1-391/512–826/S551G/T552A). Endogenous HIF-1beta is constitutively expressed in these cells at levels in excess of HIF-alpha expression. In both cell types, HIF-1alphaDP (sHIF-1alpha ) mediated significantly greater reporter gene expression in cells exposed to 20% $O_2$, due to the presence of higher levels of biologically active HIF-1alpha (note that HIF-1alpha is normally expressed only at 1% $O_2$). These results demonstrate a constitutively-expressed and biologically active form of HIF-1alpha has been generated.

Although the invention has been described with reference to the presently preferred embodiments, it should be understood that various modifications can be made without departing from the spirit of the invention. Accordingly, the invention is limited only by the following claims.

What is claimed is:

1. An isolated nucleic acid molecule encoding a polypeptide comprising a polypeptide consisting of
   amino acid residues 1–391 and 521–826 of SEQ ID NO.2;
   amino acid residues 1–391 and 549–826 of SEQ ID NO.2;
   amino acid residues 1–391 and 576–826 of SEQ ID NO.2;
   amino acid residues 1–391 and 429–826 of SEQ ID NO.2, wherein amino acid residue 551 is no longer serine and amino acid residue 552 is not threonine;
   amino acid residues 1–391 and 469–826 of SEQ ID NO.2, wherein amino acid residue 551 is no longer serine and amino acid residue 552 is not threonine;
   amino acid residues 1–391 and 494–826 of SEQ ID NO.2, wherein amino acid residue 551 is no longer serine and amino acid residue 552 is not threonine;
   amino acid residues 1–391 and 508–826 of SEQ ID NO.2, wherein amino acid residue 551 is no longer serine and amino acid residue 552 is not threonine;
   amino acid residues 1–391 and 512–826 of SEQ ID NO.2, wherein amino acid residue 551 is no longer serine and amino acid residue 552 is not threonine; or
   amino acid residues 1–391 and 517–826 of SEQ ID NO.2, wherein amino acid residue 551 is no longer serine and amino acid residue 552 is not threonine.

2. An expression vector comprising the nucleic acid molecule of claim 1.

3. A method for increasing expression of a hypoxia inducible gene in a cell comprising contacting the cell in vitro with an expression vector of claim 2 under conditions that allow expression of the nucleic acid molecule contained in the vector thereby providing for increased expression of a hypoxia inducible gene in the cell.

4. The method of claim 3, wherein the hypoxia inducible gene is vascular endothelial growth factor, erythropoietin, heme oxygenase-1, inducible nitric oxide synthase, aldolase A, enolase 1, lactate dehydrogenase A, phosphofructokinase I, phosphoglycerate kinase 1, insulin-like growth factor-2, or insulin-like growth factor binding protein.

5. A method for providing constitutive expression of a hypoxia inducible factor in a cell comprising contacting the cell in vitro with the nucleic acid molecule of claim 1, under conditions that allow expression of the nucleic acid molecule, thereby providing constitutive expression of a hypoxia inducible factor.

6. A method for reducing hypoxia or ischemia-related tissue damage in a subject comprising administering at a site of hypoxia or ischemia damage in the subject a therapeutically effective amount of the nucleic acid molecule of claim 1, in a pharmaceutically acceptable carrier, thereby reducing the tissue damage.

7. The method of claim 6, wherein the hypoxia or ischemia-related-tissue damage is due to a disorder of the cerebral, coronary or peripheral circulation.

8. An isolated nucleic acid molecule comprising a polynucleotide encoding a stable form of human hypoxia-inducible factor-1apha (sHIF-1alpha ), said sHIF-1alpha comprising a sequence as set forth in SEQ ID NO:2, except wherein amino acid residues 392 to 428 of SEQ ID NO:2 are deleted therefrom, amino acid residue 551 of SEQ ID NO:2 is changed from a serine to any other amino acid, and amino acid residue 552 of SEQ ID NO:2 is changed from a threonine to any other amino acid.

9. The nucleic acid molecule of claim 8, further comprising an expression control sequence operably linked thereto.

10. The nucleic acid molecule of claim 9, wherein the expression control sequence is a promoter.

11. The nucleic acid molecule of claim 10, wherein the promoter is tissue specific.

12. An expression vector containing the nucleic acid molecule of claim 8.

13. The vector of claim 12, wherein the vector is a plasmid.

14. The vector of claim 12, wherein the vector is a viral vector.

15. The vector of claim 14, wherein the vector is a retroviral vector.

16. An isolated host cell containing the vector of claim 12.

17. An isolated host cell of claim 14, wherein the cell is a eukaryotic cell.

18. An isolated host cell of claim 14, wherein the cell is a prokaryotic cell.

19. A method of inducing angiogenesis in a tissue of a mammal, comprising administering at the tissue of the mammal a therapeutically effective amount of a nucleotide sequence comprising an expression control sequence operatively linked to a polynucleotide encoding a polypeptide having a sequence as set forth in SEQ ID NO:2, except wherein amino acid residues 392 to 428 of SEQ ID NO:2 are deleted therefrom, amino acid residue 551 of SEQ ID NO:2 is changed from a serine to any other amino acid, and amino acid residue 552 of SEQ ID NO:2 is changed from a threonine to any other amino acid.

20. The method of claim 19, wherein amino acid 551 is changed from a serine to a glycine.

21. The method of claim 19, wherein amino acid 552 is changed from a threonine to an alanine.

22. A formulation for administration of a polynucleotide encoding stable human hypoxia-inducible factor-1apha (HIF-1alpha ) to a patient having hypoxia related tissue damage, comprising:
   (a) a therapeutically effective amount of a nucleic acid sequence comprising an expression control sequence operatively linked to a polynucleotide encoding a polypeptide having a sequence as set forth in SEQ ID NO:2, except wherein amino acid residues 392 to 428 of SEQ ID NO:2 are deleted therefrom, amino acid residue 551 of SEQ ID NO:2 is changed from a serine to any other amino acid, and amino acid residue 552 of SEQ ID NO:2 is changed from a threonine to any other amino acid; and (b) a pharmaceutically acceptable carrier.

23. The formulation of claim 22, wherein the carrier is a liposome.

24. The formulation of claim 22, wherein amino acid 551 is changed from a serine to a glycine.

25. The formulation of claim 22, wherein amino acid 552 is changed from a threonine to an alanine.

26. The method of claim 19, wherein the mammal is a human.

* * * * *

SEQUENCE LISTING

<160> NUMBER OF SEQ ID NOS: 2

<210> SEQ ID NO 1
<211> LENGTH: 3736
<212> TYPE: DNA
<213> ORGANISM: Homo sapiens
<220> FEATURE:
<221> NAME/KEY: CDS
<222> LOCATION: (29)...(2509)

<400> SEQUENCE: 1
gtgaagacat cgcggggacc gattcacc atg gag ggc gcc ggc ggc gcg aac      52

```
                    Met Glu Gly Ala Gly Gly Ala Asn
                     1                   5 gac aag aaa aag ata agt tct gaa cgt cga aaa gaa aag tct cga gat    100
Asp Lys Lys Lys Ile Ser Ser Glu Arg Arg Lys Glu Lys Ser Arg Asp
     10              15                  20 gca gcc aga tct cgg cga agt aaa gaa tct gaa gtt ttt tat gag ctt    148
Ala Ala Arg Ser Arg Arg Ser Lys Glu Ser Glu Val Phe Tyr Glu Leu
 25              30                  35                      40 gct cat cag ttg cca ctt cca cat aat gtg agt tcg cat ctt gat aag    196
Ala His Gln Leu Pro Leu Pro His Asn Val Ser Ser His Leu Asp Lys
             45                  50                  55 gcc tct gtg atg agg ctt acc atc agc tat ttg cgt gtg agg aaa ctt    244
Ala Ser Val Met Arg Leu Thr Ile Ser Tyr Leu Arg Val Arg Lys Leu
                 60                  65                  70 ctg gat gct ggt gat ttg gat att gaa gat gac atg aaa gca cag atg    292
Leu Asp Ala Gly Asp Leu Asp Ile Glu Asp Asp Met Lys Ala Gln Met
         75                  80                  85 aat tgc ttt tat ttg aaa gcc ttg gat ggt ttt gtt atg gtt ctc aca    340
Asn Cys Phe Tyr Leu Lys Ala Leu Asp Gly Phe Val Met Val Leu Thr
         90                  95                 100 gat gat ggt gac atg att tac att tct gat aat gtg aac aaa tac atg    388
Asp Asp Gly Asp Met Ile Tyr Ile Ser Asp Asn Val Asn Lys Tyr Met
105                 110                 115                 120 gga tta act cag ttt gaa cta act gga cac agt gtg ttt gat ttt act    436
Gly Leu Thr Gln Phe Glu Leu Thr Gly His Ser Val Phe Asp Phe Thr
                125                 130                 135 cat cca tgt gac cat gag gaa atg aga gaa atg ctt aca cac aga aat    484
His Pro Cys Asp His Glu Glu Met Arg Glu Met Leu Thr His Arg Asn
            140                 145                 150 ggc ctt gtg aaa aag ggt aaa gaa caa aac aca cag cga agc ttt ttt    532
Gly Leu Val Lys Lys Gly Lys Glu Gln Asn Thr Gln Arg Ser Phe Phe
            155                 160                 165 ctc aga atg aag tgt acc cta act agc cga gga aga act atg aac ata    580
Leu Arg Met Lys Cys Thr Leu Thr Ser Arg Gly Arg Thr Met Asn Ile
        170                 175                 180 aag tct gca aca tgg aag gta ttg cac tgc aca ggc cac att cac gta    628
Lys Ser Ala Thr Trp Lys Val Leu His Cys Thr Gly His Ile His Val
185                 190                 195                 200 tat gat acc aac agt aac caa cct cag tgt ggg tat aag aaa cca cct    676
Tyr Asp Thr Asn Ser Asn Gln Pro Gln Cys Gly Tyr Lys Lys Pro Pro
                205                 210                 215 atg acc tgc ttg gtg ctg att tgt gaa ccc att cct cac cca tca aat    724
Met Thr Cys Leu Val Leu Ile Cys Glu Pro Ile Pro His Pro Ser Asn
            220                 225                 230 att gaa att cct tta gat agc aag act ttc ctc agt cga cac agc ctg    772
Ile Glu Ile Pro Leu Asp Ser Lys Thr Phe Leu Ser Arg His Ser Leu
            235                 240                 245 gat atg aaa ttt tct tat tgt gat gaa aga att acc gaa ttg atg gga    820
Asp Met Lys Phe Ser Tyr Cys Asp Glu Arg Ile Thr Glu Leu Met Gly
        250                 255                 260 tat gag cca gaa gaa ctt tta ggc cgc tca att tat gaa tat tat cat    868
Tyr Glu Pro Glu Glu Leu Leu Gly Arg Ser Ile Tyr Glu Tyr Tyr His
265                 270                 275                 280 gct ttg gac tct gat cat ctg acc aaa act cat cat gat atg ttt act    916
Ala Leu Asp Ser Asp His Leu Thr Lys Thr His His Asp Met Phe Thr
                285                 290                 295 aaa gga caa gtc acc aca gga cag tac agg atg ctt gcc aaa aga ggt    964
Lys Gly Gln Val Thr Thr Gly Gln Tyr Arg Met Leu Ala Lys Arg Gly
                300                 305                 310
```

| | | |
|---|---|---|
| gga tat gtc tgg gtt gaa act caa gca act gtc ata tat aac acc aag<br>Gly Tyr Val Trp Val Glu Thr Gln Ala Thr Val Ile Tyr Asn Thr Lys<br>315 320 325 | | 1012 |
| aat tct caa cca cag tgc att gta tgt gtg aat tac gtt gtg agt ggt<br>Asn Ser Gln Pro Gln Cys Ile Val Cys Val Asn Tyr Val Val Ser Gly<br>330 335 340 | | 1060 |
| att att cag cac gac ttg att ttc tcc ctt caa caa aca gaa tgt gtc<br>Ile Ile Gln His Asp Leu Ile Phe Ser Leu Gln Gln Thr Glu Cys Val<br>345 350 355 360 | | 1108 |
| ctt aaa ccg gtt gaa tct tca gat atg aaa atg act cag cta ttc acc<br>Leu Lys Pro Val Glu Ser Ser Asp Met Lys Met Thr Gln Leu Phe Thr<br>365 370 375 | | 1156 |
| aaa gtt gaa tca gaa gat aca agt agc ctc ttt gac aaa ctt aag aag<br>Lys Val Glu Ser Glu Asp Thr Ser Ser Leu Phe Asp Lys Leu Lys Lys<br>380 385 390 | | 1204 |
| gaa cct gat gct tta act ttg ctg gcc cca gcc gct gga gac aca atc<br>Glu Pro Asp Ala Leu Thr Leu Leu Ala Pro Ala Ala Gly Asp Thr Ile<br>395 400 405 | | 1252 |
| ata tct tta gat ttt ggc agc aac gac aca gaa act gat gac cag caa<br>Ile Ser Leu Asp Phe Gly Ser Asn Asp Thr Glu Thr Asp Asp Gln Gln<br>410 415 420 | | 1300 |
| ctt gag gaa gta cca tta tat aat gat gta atg ctc ccc tca ccc aac<br>Leu Glu Glu Val Pro Leu Tyr Asn Asp Val Met Leu Pro Ser Pro Asn<br>425 430 435 440 | | 1348 |
| gaa aaa tta cag aat ata aat ttg gca atg tct cca tta ccc acc gct<br>Glu Lys Leu Gln Asn Ile Asn Leu Ala Met Ser Pro Leu Pro Thr Ala<br>445 450 455 | | 1396 |
| gaa acg cca aag cca ctt cga agt agt gct gac cct gca ctc aat caa<br>Glu Thr Pro Lys Pro Leu Arg Ser Ser Ala Asp Pro Ala Leu Asn Gln<br>460 465 470 | | 1444 |
| gaa gtt gca tta aaa tta gaa cca aat cca gag tca ctg gaa ctt tct<br>Glu Val Ala Leu Lys Leu Glu Pro Asn Pro Glu Ser Leu Glu Leu Ser<br>475 480 485 | | 1492 |
| ttt acc atg ccc cag att cag gat cag aca cct agt cct tcc gat gga<br>Phe Thr Met Pro Gln Ile Gln Asp Gln Thr Pro Ser Pro Ser Asp Gly<br>490 495 500 | | 1540 |
| agc act aga caa agt tca cct gag cct aat agt ccc agt gaa tat tgt<br>Ser Thr Arg Gln Ser Ser Pro Glu Pro Asn Ser Pro Ser Glu Tyr Cys<br>505 510 515 520 | | 1588 |
| ttt tat gtg gat agt gat atg gtc aat gaa ttc aag ttg gaa ttg gta<br>Phe Tyr Val Asp Ser Asp Met Val Asn Glu Phe Lys Leu Glu Leu Val<br>525 530 535 | | 1636 |
| gaa aaa ctt ttt gct gaa gac aca gaa gca aag aac cca ttt tct act<br>Glu Lys Leu Phe Ala Glu Asp Thr Glu Ala Lys Asn Pro Phe Ser Thr<br>540 545 550 | | 1684 |
| cag gac aca gat tta gac ttg gag atg tta gct ccc tat atc cca atg<br>Gln Asp Thr Asp Leu Asp Leu Glu Met Leu Ala Pro Tyr Ile Pro Met<br>555 560 565 | | 1732 |
| gat gat gac ttc cag tta cgt tcc ttc gat cag ttg tca cca tta gaa<br>Asp Asp Asp Phe Gln Leu Arg Ser Phe Asp Gln Leu Ser Pro Leu Glu<br>570 575 580 | | 1780 |
| agc agt tcc gca agc cct gaa agc gca agt cct caa agc aca gtt aca<br>Ser Ser Ser Ala Ser Pro Glu Ser Ala Ser Pro Gln Ser Thr Val Thr<br>585 590 595 600 | | 1828 |
| gta ttc cag cag act caa ata caa gaa cct act gct aat gcc acc act<br>Val Phe Gln Gln Thr Gln Ile Gln Glu Pro Thr Ala Asn Ala Thr Thr<br>605 610 615 | | 1876 |
| acc act gcc acc act gat gaa tta aaa aca gtg aca aaa gac cgt atg<br>Thr Thr Ala Thr Thr Asp Glu Leu Lys Thr Val Thr Lys Asp Arg Met<br>620 625 630 | | 1924 |

```
gaa gac att aaa ata ttg att gca tct cca tct cct acc cac ata cat    1972
Glu Asp Ile Lys Ile Leu Ile Ala Ser Pro Ser Pro Thr His Ile His
            635                 640                 645 aaa gaa act act agt gcc aca tca tca cca tat aga gat act caa agt    2020
Lys Glu Thr Thr Ser Ala Thr Ser Ser Pro Tyr Arg Asp Thr Gln Ser
        650                 655                 660 cgg aca gcc tca cca aac aga gca gga aaa gga gtc ata gaa cag aca    2068
Arg Thr Ala Ser Pro Asn Arg Ala Gly Lys Gly Val Ile Glu Gln Thr
665                 670                 675                 680 gaa aaa tct cat cca aga agc cct aac gtg tta tct gtc gct ttg agt    2116
Glu Lys Ser His Pro Arg Ser Pro Asn Val Leu Ser Val Ala Leu Ser
                685                 690                 695 caa aga act aca gtt cct gag gaa gaa cta aat cca aag ata cta gct    2164
Gln Arg Thr Thr Val Pro Glu Glu Glu Leu Asn Pro Lys Ile Leu Ala
            700                 705                 710 ttg cag aat gct cag aga aag cga aaa atg gaa cat gat ggt tca ctt    2212
Leu Gln Asn Ala Gln Arg Lys Arg Lys Met Glu His Asp Gly Ser Leu
        715                 720                 725 ttt caa gca gta gga att gga aca tta tta cag cag cca gac gat cat    2260
Phe Gln Ala Val Gly Ile Gly Thr Leu Leu Gln Gln Pro Asp Asp His
    730                 735                 740 gca gct act aca tca ctt tct tgg aaa cgt gta aaa gga tgc aaa tct    2308
Ala Ala Thr Thr Ser Leu Ser Trp Lys Arg Val Lys Gly Cys Lys Ser
745                 750                 755                 760 agt gaa cag aat gga atg gag caa aag aca att att tta ata ccc tct    2356
Ser Glu Gln Asn Gly Met Glu Gln Lys Thr Ile Ile Leu Ile Pro Ser
                765                 770                 775 gat tta gca tgt aga ctg ctg ggg caa tca atg gat gaa agt gga tta    2404
Asp Leu Ala Cys Arg Leu Leu Gly Gln Ser Met Asp Glu Ser Gly Leu
            780                 785                 790 cca cag ctg acc agt tat gat tgt gaa gtt aat gct cct ata caa ggc    2452
Pro Gln Leu Thr Ser Tyr Asp Cys Glu Val Asn Ala Pro Ile Gln Gly
        795                 800                 805 agc aga aac cta ctg cag ggt gaa gaa tta ctc aga gct ttg gat caa    2500
Ser Arg Asn Leu Leu Gln Gly Glu Glu Leu Leu Arg Ala Leu Asp Gln
    810                 815                 820 gtt aac tga gcttttctt aatttcattc cttttttgg acactggtgg             2549
Val Asn  *
825 ctcactacct aaagcagtct atttatattt tctacatcta attttagaag cctggctaca    2609 atactgcaca aacttggtta gttcaatttt tgatcccctt tctacttaat ttacattaat    2669 gctctttttt agtatgttct ttaatgctgg atcacagaca gctcattttc tcagtttttt    2729 ggtatttaaa ccattgcatt gcagtagcat cattaattaa aaaatgcacc ttttttattta    2789 tttattttg gctagggagt ttatcccttt ttcgaattat ttttaagaag atgccaatat    2849 aattttgta agaaggcagt aacctttcat catgatcata ggcagttgaa aaatttttac    2909 acctttttt tcacaaattt tacataaata ataatgcttt gccagcagta cgtggtagcc    2969 acaattgcac aatatatttt cttaaaaaat accagcagtt actcatggaa tatattctgc    3029 gtttataaaa ctagttttta agaagaaatt ttttttggcc tatgaaattg ttaaacaact    3089 ggaacatgac attgttaatc atataataat gattcttaaa tgctgtatgg tttattattt    3149 aaatgggtaa agccatttac ataatataga aagatatgca tatatctaga aggtatgtgg    3209 catttatttg gataaaattc tcaattcaga gaaatcaaat ctgatgtttc tatagtcact    3269 ttgccagctc aaaagaaaac aatacccctat gtagttgtgg aagtttatgc taatattgtg    3329
```

-continued

```
taactgatat taaacctaaa tgttctgcct accctgttgg tataaagata ttttgagcag    3389
actgtaaaca agaaaaaaaa aaaatcatgc attcttagca aaattgccta gtatgttaat    3449
ttgctcaaaa tacaatgttt gattttatgc actttgtcgc tattaacatc cttttttca    3509 tgtagatttc ataattgag taattttaga agcattattt taggaatata tagttgtcaa    3569
aaacagtaaa tatcttgttt tttctatgta cattgtacaa attttcatt ccttttgctc    3629 tttgtggttg gatctaacac taactgtatt gttttgttac atcaaataaa catcttctgt    3689
ggaaaaaaaa aaaaaaaaaa aaaaaaaaaa aaaaaaaaa aaaaaaa                   3736
```

<210> SEQ ID NO 2
<211> LENGTH: 826
<212> TYPE: PRT
<213> ORGANISM: Homo sapiens

<400> SEQUENCE: 2

```
Met Glu Gly Ala Gly Gly Ala Asn Asp Lys Lys Lys Ile Ser Ser Glu
 1               5                  10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Asp Leu Asp Ile
 65              70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300
```

-continued

```
Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
            325                 330                 335

Cys Val Asn Tyr Val Val Ser Gly Ile Ile Gln His Asp Leu Ile Phe
                340                 345                 350

Ser Leu Gln Gln Thr Glu Cys Val Leu Lys Pro Val Glu Ser Ser Asp
            355                 360                 365

Met Lys Met Thr Gln Leu Phe Thr Lys Val Glu Ser Glu Asp Thr Ser
        370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685

Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
```

-continued

```
                        725                     730                     735
Leu Leu Gln Gln Pro Asp Asp His Ala Ala Thr Thr Ser Leu Ser Trp
            740                     745                 750

Lys Arg Val Lys Gly Cys Lys Ser Ser Glu Gln Asn Gly Met Glu Gln
        755                     760                 765

Lys Thr Ile Ile Leu Ile Pro Ser Asp Leu Ala Cys Arg Leu Leu Gly
    770                     775                 780

Gln Ser Met Asp Glu Ser Gly Leu Pro Gln Leu Thr Ser Tyr Asp Cys
785                     790                     795                 800

Glu Val Asn Ala Pro Ile Gln Gly Ser Arg Asn Leu Leu Gln Gly Glu
                805                     810                     815

Glu Leu Leu Arg Ala Leu Asp Gln Val Asn
            820                     825
```